(12) United States Patent
Jin

(10) Patent No.: US 8,334,105 B2
(45) Date of Patent: Dec. 18, 2012

(54) METHODS FOR TREATING CARDIAC DISEASE BY MODIFYING AN N-TERMINAL DOMAIN OF TROPONIN I

(75) Inventor: Jian-Ping Jin, Northbrook, IL (US)

(73) Assignee: Northshore University Healthsystem, Evanston, IL (US)

( * ) Notice: Subject to any disclaimer, the term of this patent is extended or adjusted under 35 U.S.C. 154(b) by 435 days.

(21) Appl. No.: 12/350,104

(22) Filed: Jan. 7, 2009

(65) Prior Publication Data

US 2009/0181405 A1 Jul. 16, 2009

Related U.S. Application Data

(62) Division of application No. 11/311,472, filed on Dec. 19, 2005, now abandoned.

(60) Provisional application No. 60/638,073, filed on Dec. 20, 2004.

(51) Int. Cl.
*G01N 33/53* (2006.01)
*G01N 31/00* (2006.01)

(52) U.S. Cl. ........ 435/7.21; 435/7.1; 436/501; 436/506; 436/518; 530/300; 530/350

(58) Field of Classification Search .................. None
See application file for complete search history.

(56) References Cited

U.S. PATENT DOCUMENTS

| | | | |
|---|---|---|---|
| 4,179,337 A | 12/1979 | Davis et al. | |
| 4,301,144 A | 11/1981 | Iwashita et al. | |
| 4,496,689 A | 1/1985 | Mitra | |
| 4,640,835 A | 2/1987 | Shimizu et al. | |
| 4,670,417 A | 6/1987 | Iwasaki et al. | |
| 4,791,192 A | 12/1988 | Nakagawa et al. | |
| 5,530,101 A | 6/1996 | Queen et al. | |
| 5,565,332 A | 10/1996 | Hoogenboom et al. | |
| 5,585,089 A | 12/1996 | Queen et al. | |
| 5,693,761 A | 12/1997 | Queen et al. | |
| 5,693,762 A | 12/1997 | Queen et al. | |
| 5,766,886 A | 6/1998 | Studnicka et al. | |
| 5,869,619 A | 2/1999 | Studnicka | |
| 5,885,793 A | 3/1999 | Griffiths et al. | |
| 6,054,297 A | 4/2000 | Carter et al. | |
| 6,072,035 A | 6/2000 | Hardman et al. | |
| 6,133,426 A | 10/2000 | Gonzalez et al. | |

FOREIGN PATENT DOCUMENTS

| | | |
|---|---|---|
| WO | WO-94/15217 | 7/1994 |
| WO | WO-97/09433 | 3/1997 |
| WO | WO-99/10494 | 4/1999 |
| WO | WO-00/23585 | 4/2000 |

OTHER PUBLICATIONS

Barbato et al., Proteolytic N-terminal truncation of cardiac troponin I enhances ventricular diastolic function, J. Biol. Chem., 280:6602-6609, 2005.
Barbato et al., Rapid effects of aldosterone and spironolactone in the isolated working rat heart, Hypertension, 40:130-135, 2001.
Biesiadecki et al., An R111C polymorphism in wild turkey cardiac troponin I accompanying the dilated cardiomyopathy-related abnormal splicing variant of cardiac troponin T with potentially compensatory effects, J. Biol. Chem., 279:13825-13832, 2004.
Biesiadecki et al., Exon skipping in cardiac troponin T of turkeys with inherited dilated cardiomyopathy, J. Biol. Chem., 277:18459-18468, 2002.
Brazier et al., The adequacy of subendocardial oxygen delivery: the interaction of determinants of flow, arterial oxygen content and myocardial oxygen need, Circulation, 49:968-977, 1974.
Buckberg et al., Experimental subendocardial ischemia in dogs with normal coronary arteries, Circ. Res., 30:67-81, 1972.
Bungo et al., Echocardiographic evaluation of space shuttle crewmembers, J. Appl. Physio 62:278-283, 1987.
Burton et al., Two mutations in troponin I that cause hypertrophic cardiomyopathy have contrasting effects on cardiac muscle contractility, Biochem. J., 362:443-451, 2002.
Chandra et al., Effects of protein kinase A phosphorylation on signaling between cardiac troponin I and the N-terminal domain of cardiac troponin C, Biochem., 36:13305-13311, 1997.
Chemla et al., Short-term variability of pulse pressure and systolic and diastolic time in heart transplant recipients, Am. J. Physiol. Heart Circ. Physiol., 279, H122-H129, 2000.
Chothia et al., Canonical structures for the hypervariable regions of immunoglobulins, J. Mol. Biol., 196:901-917, 1986.
Chothia et al., Conformations of immunoglobulin hypervariable regions, Nature, 342:877-883, 1989.
Chowdhury, et al., Improving antibody affinity by mimicking somatic hypermutation in vitro, Nature Biotech., 17:568-572, 1999.
Co et al., Genetically engineered deglycosylation of the variable domain increases the affinity of an anti-CD33 monoclonal antibody, Mol. Immunol., 30:1361-1367, 1993.

(Continued)

*Primary Examiner* — Lisa Cook
(74) *Attorney, Agent, or Firm* — Marshall, Gerstein & Borun LLP

(57) ABSTRACT

The invention provides methods for identifying modulators of cardiac troponin I activity as well as methods for using N-terminally truncated forms of cTnI to monitor the function of the circulatory system in general, and the heart in particular, of an organism such as man. Additionally, the invention provides methods of treating circulatory diseases, disorders or conditions, such as cardiac diseases and conditions, by administering a therapeutically effective amount of a modulator of the N-terminal structure of cTnI, such as a molecule capable of binding to the N-terminus of full-length cTnI, a molecule that modulates cTnI phosphorylation and/or N-terminal proteolytic cleavage, or by administering N-terminally truncated cTnI or a polynucleotide encoding that protein or polypeptide.

20 Claims, 16 Drawing Sheets

OTHER PUBLICATIONS

Figure 1:
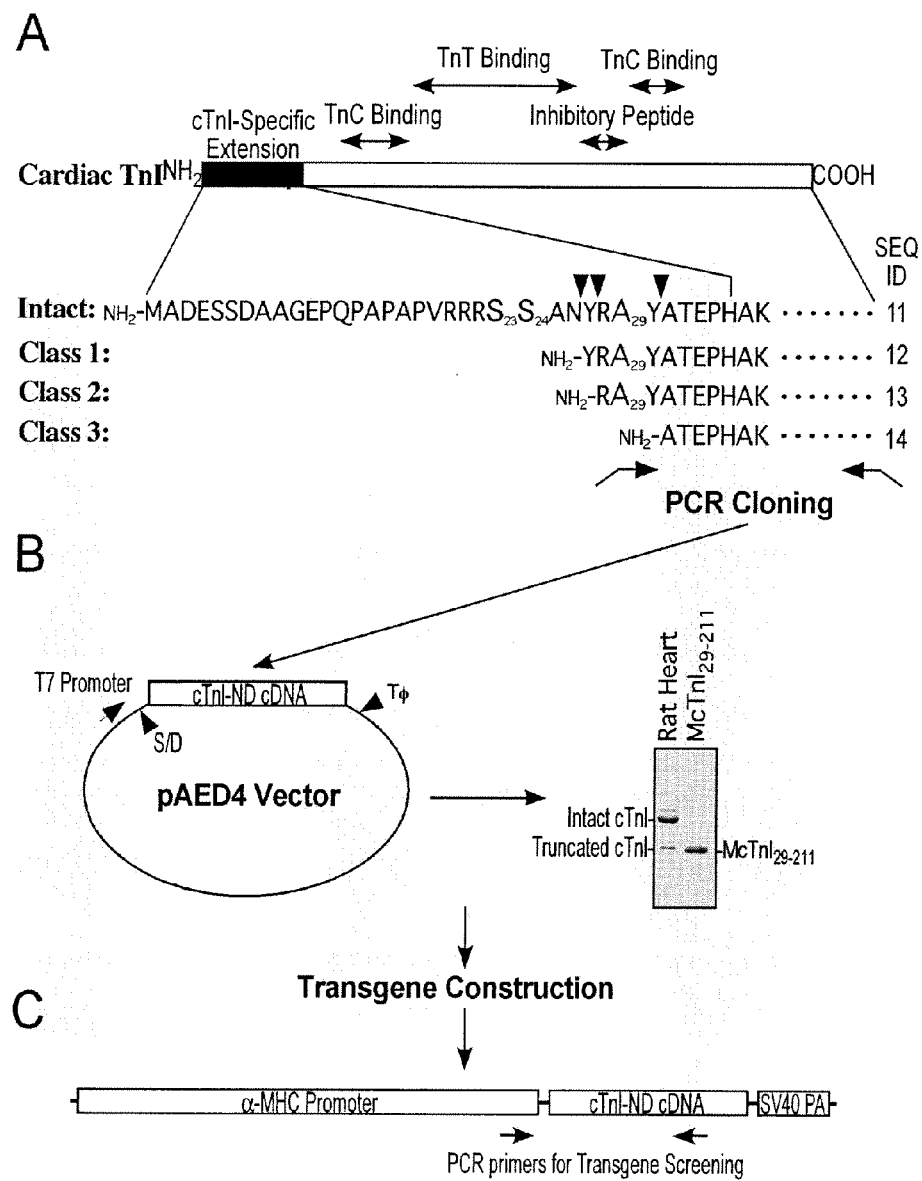

Convertino et al., Cardiovascular physiology: effects of microgravity, J. Fla. Med. Assoc., 79:517-524, 1992.

Convertino et al., Effect of simulated microgravity on cardiopulmonary baroreflex control of forearm vascular resistance, Am. J. Physiol., 266:R1962-R1969, 1994.

Convertino et al., Evidence for increased beta-adrenoreceptor responsiveness induced by 14 days of simulated microgravity in humans, Am. J. Physiol., 273:R93-R99, 1997.

Cooke, The mechanism of muscle contraction, CRC Crit. Rev. Biochem., 21:53-118, 1986.

Cote et al., Generation of human monoclonal antibodies reactive with cellular antigens, Proc. Natl. Acad. Sci. (USA), 80:2026-2030, 1983.

Dohet et al., Reconstitution of skinned cardiac fibres with human recombinant cardiac troponin-I mutants and troponin-C, FEBS Lett., 377:131-134, 1995.

Dunlap et al., Decreased $Ca^{2+}$ sensitivity of isometric tension in skinned cardiac myocytes from tail-suspended rats, J. Appl. Physiol., 80:1612-1617, 1996.

Fabiato, Myoplasmic free calcium concentration reached during the twitch of an intact isolated cardiac cell and during calcium-induced release of calcium from the sarcoplasmic reticulum of a skinned cardiac cell from the adult rat or rabbit ventricle, J. Gen. Physiol., 78:457-497, 1981.

Duncan et al., Cardiovascular response to sudden strenuous exercise, Basic Res. Cardiol., 82:226-232, 1987.

Fentzke et al., Impaired cardiomyocyte relaxation and diastolic function in transgenic mice expressing slow skeletal troponin I in the heart, J. Physiol., 517:143-157, 1999.

Ferro et al., Relation between diastolic perfusion time and coronary artery stenosis during stress-induced myocardial ischemia, Circulation, 92:342-347, 1995.

Fiske et al., The colorimetric determination of phosphorus, J. Biol. Chem., 66:375-400, 1925.

Gaffney et al, Cardiovascular deconditioning produced by 20 hours of bedrest with head-down tilt (−5 degrees) in middle-aged healthy men, Am. J. Cardiol., 56:634-638, 1985.

Gauthier et al., Determination of function in the isolated working mouse heart: issues in experimental design, J. Mol. Cell. Cardiol., 30:453-461, 1998.

Genbank accession No. AAC14461, *Homo sapiens* troponin I, Apr. 22, 1998.

Genbank accession No. BT019517, *Homo sapiens* troponin I, cardiac mRNA, complete cds., Oct. 28, 2004.

Gilliland et al., Elimination of the immunogenicity of therapeutic antibodies, J. Immunol., 162:3663-3671,1999.

Gordon et al., Regulation of contraction in striated muscle, Physiol. Rev., 80:853-924, 2000.

Goto et al., Decreased contractile efficiency and increased nonmechanical energy cost in hyperthyroid rabbit heart. Relation between O2 consumption and systolic pressure-volume area or force-time integral, Circ. Res. 66:999-1011, 1990.

Griffiths et al, Isolation of high affinity human antibodies directly from large synthetic repertoires, EMBO J. 13:3245-3260, 1994.

Guo et al., Mutagenesis of cardiac troponin I: role of the unique $NH_2$-terminal peptide in myofilament activation, J. Biol. Chem., 269:15210-15216, 1994.

Guyton et al., Central venous pressure: physiological significance and clinical implications, Am. Heart J., 86:431-437, 1973.

Hisano et al., Correlation of force-length area with oxygen consumption in ferret papillary muscle, Circ Res., 61:318-328, 1987.

Hoffman et al., The myocardial supply:demand ratio—a critical review, Am. J. Cardiol., 41:327-332, 1978.

Hoogenboom et al., By-passing immunization: human antibodies from synthetic repertoires of germline VH gene segments rearranged in vitro, J. Mol. Biol., 227:381-388, 1992.

Hope et al., Comparison of generalized and gender-specific transfer functions for the derivation of aortic waveforms, Am. J. Physiol. Heart Circ. Physiol., 283:H1150-1156, 2002.

Huang et al., Fast skeletal muscle troponin T increases the cooperativity of transgenic mouse cardiac muscle contraction, J. Physiol., 520:231-242, 1999.

Hudson, Recombinant antibody fragments, Curr. Opin. Biotech., 9:395-402, 1999.

Jin et al., A role for serine-175 in modulating the molecular conformation of calponin, Biochem. J., 350:579-588, 2000.

Jin et al., Conformational modulation of slow skeletal muscle troponin T by an NH2-terminal metal-binding extension, Am. J. Physiol. Cell. Physiol., 279:C1067-C1077, 2000.

Jin et al., Expression of cDNAs encoding mouse cardiac troponin T isoforms: characterization of a large sample of independent clones, Gene, 168:217-221, 1996.

Jin et al., Modulation of troponin T molecular conformation and flexibility by metal ion binding to the NH2-terminal variable region, Biochem., 39:11702-11713, 2000.

Jin et al., The highly conserved COOH terminus of troponin I forms a $Ca^{2+}$-modulated allosteric domain in the troponin complex, Biochem., 40:2623-2631, 2001.

Jin, Alternative RNA splicing-generated cardiac troponin T isoform switching: a non-heartrestricted genetic programming synchronized in developing cardiac and skeletal muscles, Biochem. Biophys. Res. Commun., 225:883-889, 1996.

Johnson et al., Kabat database and its applications: 30 years after the first variability plot, Nucl. Acids Res., 28:214-218, 2000.

Kashihara et al., Effects of mild supine exercise during 20 days bed rest on maximal oxygen uptake rate in young humans, Acta Physiol. Scand., 150:19-26, 1994.

Kass et al., Adverse influence of systemic vascular stiffening on cardiac dysfunction and adaptation to acute coronary occlusion, Circulation, 93:1533-1541, 1996.

Kessler et al., Cardiovascular findings in quadriplegic and paraplegic patients and in normal subjects, Am. J. Cardiol., 58:525-530, 1986.

Khairallah et al., Profiling substrate fluxes in the isolated working mouse heart using 13C-labeled substrates: focusing on the origin and fate of pyruvate and citrate carbons, Am. J. Physiol. Heart Circ. Physiol., 286:H1461-H1470, 2004.

Kolch, Coordinating ERK/MAPK signaling through scaffolds and inhibitors, Nat. Rev. Mol. Cell Biol., 6:827-837, 2005.

Kozbor et al., The production of monoclonal antibodies from human lymphocytes, Immunol. Today, 4:72-79, 1983.

Layland et al., Essential role of troponin I in the positive inotropic response to isoprenaline in mouse hearts contracting auxotonically, J. Physiol., 556:835-847, 2004.

Leavis et al., Thin filament proteins and thin filament-linked regulation of vertebrate muscle contraction, CRC Crit. Rev. Biochem., 16:235-305, 1984.

Li et al., Interaction of cardiac troponin C with Ca(2+) sensitizer EMD 57033 and cardiac troponin I inhibitory peptide, Biochem., 39:8782-8790, 2000.

Liao et al., p38 mitogen-activated protein kinase mediates a negative inotropic effect in cardiac myocytes, Circ. Res., 90:190-196, 2002.

Lüscher et al., Applicability of cardiac troponin T and I for early risk stratification in unstable coronary artery disease, Circulation, 96:2578-2585, 1997.

MacCallum et al., Antibody-antigen interactions: contact analysis and binding site topography, J. Mol. Biol., 5:732-745, 1996.

Marks et al., By-passing immunization. Human antibodies from V-gene libraries displayed on phage, J. Mol. Biol., 222:581-597, 1991.

Martin et al., Modeling antibody hypervariable loops: a combined algorithm, Proc. Natl. Acad. Sci. (USA), 86:9268-9272, 1989.

McDonough et al., Troponin I degradation and covalent complex formation accompanies myocardial ischemia/reperfusion injury, Circ. Res., 84:9-20, 1999.

Menedez et al., Oleic acid, the main monosaturated fatty acid of olive oil, suppresses Her-*2/neu* (*erb* B-2) expression and synergistically enhances the growth inhibitory effects of trastuzumab (Herceptin™) in breast cancer cells with Her-*2/neu* oncogene amplification, Ann. Oncology, 16:359-371, 2005.

Metzger et al., Transition in cardiac contractile sensitivity to calcium during the in vitro differentiation of mouse embryonic stem cells, J. Cell. Biol., 126:701-711, 1994.

Montgomery et al., α-Adrenergic response and myofilament activity in mouse hearts lacking PKC phosphorylation sites on cardiac TnI, Am. J. Physiol. Heart Circ. Physiol., 282:H2397-2405, 2002.

Moore et al., Space shuttle inflight and postflight fluid shifts measured by leg volume changes, Aviat. Space Environ. Med., 58:A91-A96 1987.

Mullan et al., Ascorbic acid reduces blood pressure and arterial stiffness in type 2 diabetes, Hypertension, 40:804-809, 2002.

Mullinax et al., Identification of human antibody fragment clones specific for tetanus toxoid in a bacteriophage lambda immunoexpression library, Proc. Natl. Acad. Sci. (USA), 87:8095-8099, 1990.

Murphy et al., Transgenic mouse model of stunned myocardium, Science, 287:488-491, 2000.

Neely et al., Effect of pressure development on oxygen consumption by isolated rat heart, Am. J. Physiol., 212:804-814, 1967.

O'Rourke et al., Pulse wave analysis, Hypertension, 14:S147-S157, 1996.

Parazynski et al., Transcapillary fluid shifts in tissues of the head and neck during and after simulated microgravity, J. Appl. Physiol., 71:2469-2475, 1991.

Perhonen et al., Cardiac atrophy after bed rest and spaceflight, J. Appl. Physiol., 91:645-653, 2001.

Perry, Troponin I: inhibitor or facilitator, Mol. Cell. Biochem., 190:9-32, 1999.

Rarick et al., An essential myosin light chain peptide induces supramaximal stimulation of cardiac myofibrillar ATPase activity, J. Biol. Chem., 271:27039-27043, 1996.

Rarick et al., The C terminus of cardiac troponin I is essential for full inhibitory activity and $Ca^{2+}$ sensitivity of rat myofibrils, J. Biol. Chem., 272:26887-26892, 1997.

Robertson et al., The effect of troponin I phosphorylation on the $Ca^{2+}$-binding properties of the $Ca^{2+}$-regulatory site of bovine cardiac troponin, J. Biol. Chem., 257:260-263, 1982.

Roguska et al., A comparison of two murine monoclonal antibodies humanized by CDR-grafting and variable domain resurfacing, Protein Eng., 9:895-904, 1996.

Saggin et al., Troponin I switching in the developing heart, J. Biol. Chem., 264:16299-16302, 1989.

Saldanha et al., A single backmutation in the human kIV framework of a previously unsuccessfully humanized antibody restores the binding activity and increases the secretion in cos cells, Mol. Immunol., 36:709-719, 1999.

Sangha et al., Simulated microgravity upregulates an endothelial vasoconstrictor prostaglandin, J. Appl. Physiol., 91:789-796, 2001.

Schuurs et al., Enzyme-immunoassay, Clin. Chim. Acta, 81:1-40, 1977.

Solaro et al., Cardiac relaxation and myofibrillar interactions with phosphate and vanadate, Eur. Heart J., Supplement A:21-27, 1980.

Solaro et al., The purification of cardiac myofibrils with Triton X-100, Biochim. Biophys. Acta, 245:259-262, 1971.

Strauss et al., Recombinant troponin I substitution and calcium responsiveness in skinned cardiac muscle, Eur. J. Physiol., 431:853-862, 1996.

Subramaniam et al., Transgenic analysis of the thyroid-responsive elements in the alpha-cardiac myosin heavy chain gene promoter, J. Biol. Chem., 268:4331-4336, 1993.

Sulakhe et al., Regulation of phospholamban and troponin-I phosphorylation in the intact rat cardiomyocytes by adrenergic and cholinergic stimuli: roles of cyclic nucleotides, calcium, protein kinases and phosphatases and depolarization, Mol. Cell. Biochem., 149:103-126, 1995.

Takeda, Structure of the core domain of human cardiac troponin in the $Ca^{2+}$-saturated form, Nature, 424:35-41, 2003.

Tomai et al., Beneficial impact of isoflurane during coronary bypass surgery on troponin I release, G. Ital. Cardiol., 29(9):1007-1014, 1999.

Tomaselli et al., Cardiovascular dynamics during the initial period of head-down tilt, Aviat. Space Environ. Med., 58:3-8, 1987.

Vaswani et al., Humanized antibodies as potential therapeutic drugs, Ann. Allergy Asthma Immunol., 81:105-115, 1998.

Wang et al., Conformational modulation of troponin T by configuration of the $NH_2$-terminal variable region and functional effects, Biochem., 37:14519-14528, 1998.

Ward et al., Additional PKA phosphorylation sites in human cardiac troponin I, Eur. J. Biochem., 268:179-185, 2001.

Ward et al., Structural consequences of cardiac troponin I phosphorylation, J. Biol. Chem., 277:41795-41801, 2002.

Wattanapermpool et al., The unique amino-terminal peptide of cardiac troponin I regulates myofibrillar activity only when it is phosphorylated, J. Mol. Cell. Cardiol., 27:1383-1391, 1995.

Westfall et al., Gene transfer of troponin I isoforms, mutants, and chimeras, Adv. Exp. Med. Biol., 538:169-174, 2003.

Westfall et al., Slow skeletal troponin I gene transfer, expression, and myofilament incorporation enhances adult cardiac myocyte contractile function, Proc. Natl. Acad. Sci. (USA), 94:5444-5449, 1997.

Winter, Synthetic human antibodies and a strategy for protein engineering, FEBS Lett., 430:92-94, 1998.

Wu et al., Altered phosphorylation and calcium sensitivity of cardiac myofibrillar proteins during sepsis, Am. J. Physiol. Regul. Integr. Comp. Physiol., 281:R408-R416, 2001.

Yu et al., A proteolytic $NH_2$-terminal truncation of cardiac troponin I that is up-regulated in simulated microgravity, J. Biol. Chem., 276:15753-15760, 2001.

Zhang et al., Phosphorylation of both serine residues in cardiac troponin I is required to decrease the $Ca^{2+}$ affinity of cardiac troponin C, J. Biol. Chem. 270:30773-30780, 1995.

|   | I | II | III | IV | V | VI | VII | VIII | IX | X |
|---|---|---|---|---|---|---|---|---|---|---|
| A | 1 | 2 | 3 | 4 | 5 | 6 | 7 | 8 | 9 | 10 |
| B | 11 | 12 | 13 | 14 | 15 | 16 | 17 | 18 | 19 | 20 |
| C | 21 | 22 | 23 | 24 | 25 | 26 | 27 | 28 | 29 | 30 |
| D | 31 | 32 | 33 | 34 | 35 | 36 | 37 | 38 | 39 | 40 |
| E | 41 | 42 | 43 | 44 | 45 | 46 | 47 | 48 | 49 | 50 |
| F | 51 | 52 | 53 | 54 | 55 | 56 | 57 | 58 | 59 | 60 |
| G | 61 | 62 | 63 | 64 | 65 | 66 | 67 | 68 | 69 | 70 |
| H | 71 | 72 | 73 | 74 | 75 | 76 | 77 | 78 | 79 | 80 |
| I | 81 | 82 | 83 | 84 | 85 | 86 | 87 | 88 | 89 | 90 |
| J | 91 | 92 | 93 | 94 | 95 | 96 | 97 | 98 | 99 | 100 |

*FIG. 15*

SEQUENCE LISTING

```
<160> NUMBER OF SEQ ID NOS: 18

<210> SEQ ID NO 1
<211> LENGTH: 633
<212> TYPE: DNA
<213> ORGANISM: Homo sapiens

<400> SEQUENCE: 1
atggcggatg ggagcagcga tgcggctagg gaacctcgcc ctgcaccagc cccaatcaga      60
cgccgctcct ccaactaccg cgcttatgcc acggagccgc acgccaagaa aaaatctaag     120
atctccgcct cgagaaaatt gcagctgaag actctgctgc tgcagattgc aaagcaagag     180
ctggagcgag aggcggagga gcggcgcgga gagaaggggc gcgctctgag cacccgctgc     240
cagccgctgg agttggccgg gctgggcttc gcggagctgc aggacttgtg ccgacagctc     300
cacgcccgtg tggacaaggt ggatgaagag agatacgaca tagaggcaaa agtcaccaag     360
aacatcacgg agattgcaga tctgactcag aagatctttg accttcgagg caagtttaag     420
cggcccaccc tgcggagagt gaggatctct gcagatgcca tgatgcaggc gctgctgggg     480
gcccgggcta aggagtccct ggacctgcgg gcccacctca gcaggtgaa gaaggaggac     540
```

```
accgagaagg aaaaccggga ggtgggagac tggcgcaaga acatcgatgc actgagtgga    600
atggagggcc gcaagaaaaa gtttgagagc tag                                 633

<210> SEQ ID NO 2
<211> LENGTH: 210
<212> TYPE: PRT
<213> ORGANISM: Homo sapiens

<400> SEQUENCE: 2

Met Ala Asp Gly Ser Ser Asp Ala Ala Arg Glu Pro Arg Pro Ala Pro
1               5                   10                  15

Ala Pro Ile Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
        35                  40                  45

Leu Lys Thr Leu Leu Leu Gln Ile Ala Lys Gln Glu Leu Glu Arg Glu
    50                  55                  60

Ala Glu Glu Arg Arg Gly Glu Lys Gly Arg Ala Leu Ser Thr Arg Cys
65                  70                  75                  80

Gln Pro Leu Glu Leu Ala Gly Leu Gly Phe Ala Glu Leu Gln Asp Leu
                85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
        115                 120                 125

Thr Gln Lys Ile Phe Asp Leu Arg Gly Lys Phe Lys Arg Pro Thr Leu
    130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
                165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
        195                 200                 205

Glu Ser
    210

<210> SEQ ID NO 3
<211> LENGTH: 855
<212> TYPE: DNA
<213> ORGANISM: Mus musculus

<400> SEQUENCE: 3
agtgtcctca gtgaggcttg agcagcccag aggaaaccca acctctagag acctccaagg    60
tcaccaggga cacccttcca ggaccctcca ggaatctccg atcctgttct ctgcctctgg   120
agatcatcat ggctgatgag agcagcgatg cggctgggga accgcagcct gcgcctgctc   180
ctgtccgacg ccgctcctct gccaactacc gagcctatgc caccgagcca cacgccaaga   240 aaagtctaa gatctccgcc tccagaaaac ttcagttgaa gactctgatg ctgcagattg   300
cgaagcagga gatggaacga gaggcagaag agcgacgtgg agagaagggg cgcgttctga   360
ggactcgttg ccagcctttg gagttggatg ggctgggctt tgaagagctt caggacttat   420
gccgacagct tcacgctcgg gtggacaaag tggatgaaga gagatatgac gtggaagcaa   480
aagtcaccaa gaacatcact gagattgcag atctgaccca gaagatctat gacctccgtg   540
```

```
gcaagtttaa gcggcccacc ctccgaagag tgaggatctc tgcagatgcc atgatgcagg    600
cgctgctggg gacccgggcc aaggaatcct tggacctgag ggcccacctc aagcaggtga    660
agaaggagga cattgagaag gaaaaccggg aggtgggaga ctggcgcaag aatatcgatg    720
cactgagtgg catggaaggc cgcaagaaaa agtttgaggg ctgagccatg gctcccacac    780
tgtgctctga aggacgtccc tgcagaataa acctctccaa accacaaaaa aaaaaaaaaa    840
aaaaaaaaaa aaaaa                                                     855
```

<210> SEQ ID NO 4
<211> LENGTH: 211
<212> TYPE: PRT
<213> ORGANISM: Mus musculus

<400> SEQUENCE: 4

```
Met Ala Asp Glu Ser Ser Asp Ala Ala Gly Glu Pro Gln Pro Ala Pro
1               5                   10                  15

Ala Pro Val Arg Arg Ser Ser Ala Asn Tyr Arg Ala Tyr Ala Thr
            20                  25                  30

Glu Pro His Ala Lys Lys Ser Lys Ile Ser Ala Ser Arg Lys Leu
        35                  40                  45

Gln Leu Lys Thr Leu Met Leu Gln Ile Ala Lys Gln Glu Met Glu Arg
50                  55                  60

Glu Ala Glu Glu Arg Arg Gly Glu Lys Gly Arg Val Leu Arg Thr Arg
65                  70                  75                  80

Cys Gln Pro Leu Glu Leu Asp Gly Leu Gly Phe Glu Glu Leu Gln Asp
                85                  90                  95

Leu Cys Arg Gln Leu His Ala Arg Val Asp Lys Val Asp Glu Glu Arg
            100                 105                 110

Tyr Asp Val Glu Ala Lys Val Thr Lys Asn Ile Thr Glu Ile Ala Asp
        115                 120                 125

Leu Thr Gln Lys Ile Tyr Asp Leu Arg Gly Lys Phe Lys Arg Pro Thr
    130                 135                 140

Leu Arg Arg Val Arg Ile Ser Ala Asp Ala Met Met Gln Ala Leu Leu
145                 150                 155                 160

Gly Thr Arg Ala Lys Glu Ser Leu Asp Leu Arg Ala His Leu Lys Gln
                165                 170                 175

Val Lys Lys Glu Asp Ile Glu Lys Glu Asn Arg Glu Val Gly Asp Trp
            180                 185                 190

Arg Lys Asn Ile Asp Ala Leu Ser Gly Met Glu Gly Arg Lys Lys Lys
        195                 200                 205

Phe Glu Gly
    210
```

<210> SEQ ID NO 5
<211> LENGTH: 26
<212> TYPE: PRT
<213> ORGANISM: Artificial sequence
<220> FEATURE:
<223> OTHER INFORMATION: Synthetic peptide

<400> SEQUENCE: 5

```
Gly Ser Ser Asp Ala Ala Arg Glu Pro Arg Pro Ala Pro Ala Pro Ile
1               5                   10                  15

Arg Arg Arg Ser Ser Asn Tyr Arg Ala Tyr
            20                  25
```

<210> SEQ ID NO 6

```
<211> LENGTH: 4
<212> TYPE: DNA
<213> ORGANISM: Artificial Sequence
<220> FEATURE:
<223> OTHER INFORMATION: Synthetic Nucleotide

<400> SEQUENCE: 6 rgyw                                                                     4

<210> SEQ ID NO 7
<211> LENGTH: 3
<212> TYPE: DNA
<213> ORGANISM: Artificial Sequence
<220> FEATURE:
<223> OTHER INFORMATION: Synthetic Nucleotide

<400> SEQUENCE: 7 agy                                                                      3

<210> SEQ ID NO 8
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 8

Leu Glu Trp Ile Gly
1               5

<210> SEQ ID NO 9
<211> LENGTH: 3
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: May be Lysine or Arginine
<220> FEATURE:
<221> NAME/KEY: MISC_FEATURE
<222> LOCATION: (2)..(2)
<223> OTHER INFORMATION: May be Leucine, Isoleucine, Valine,
      Phenylalanine, Threonine, or Alanine
<220> FEATURE:
<221> NAME/KEY: MISC_FEATURE
<222> LOCATION: (3)..(3)
<223> OTHER INFORMATION: May be Threonine, Serine, Isoleucine, or
      Alanine

<400> SEQUENCE: 9

Xaa Xaa Xaa
1

<210> SEQ ID NO 10
<211> LENGTH: 4
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 10

Phe Gly Xaa Gly
1
```

```
<210> SEQ ID NO 11
<211> LENGTH: 37
<212> TYPE: PRT
<213> ORGANISM: Artificial Sequence
<220> FEATURE:
<223> OTHER INFORMATION: Synthetic Peptide

<400> SEQUENCE: 11

Met Ala Asp Glu Ser Ser Asp Ala Ala Gly Glu Pro Gln Pro Ala Pro
1               5                   10                  15

Ala Pro Val Arg Arg Arg Ser Ser Ala Asn Tyr Arg Ala Tyr Ala Thr
            20                  25                  30

Glu Pro His Ala Lys
        35

<210> SEQ ID NO 12
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 12

Tyr Arg Ala Tyr Ala Thr Glu Pro His Ala Lys
1               5                   10

<210> SEQ ID NO 13
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 13

Arg Ala Tyr Ala Thr Glu Pro His Ala Lys
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 14

Ala Thr Glu Pro His Ala Lys
1               5

<210> SEQ ID NO 15
<211> LENGTH: 40
<212> TYPE: PRT
<213> ORGANISM: Artificial Sequence
<220> FEATURE:
<223> OTHER INFORMATION: Synthetic Peptide

<400> SEQUENCE: 15

Met Ala Asp Glu Ser Ser Asp Ala Ala Gly Glu Pro Gln Pro Ala Pro
1               5                   10                  15

Ala Pro Val Arg Arg Arg Ser Ser Ala Asn Tyr Arg Ala Tyr Ala Thr
            20                  25                  30

Glu Pro His Ala Lys Lys Lys Ser
        35                  40

<210> SEQ ID NO 16
<211> LENGTH: 14
<212> TYPE: PRT
```

```
<213> ORGANISM: Artificial Sequence
<220> FEATURE:
<223> OTHER INFORMATION: Synthetic Peptide

<400> SEQUENCE: 16

Tyr Arg Ala Tyr Ala Thr Glu Pro His Ala Lys Lys Lys Ser
1               5                   10

<210> SEQ ID NO 17
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 17

Arg Ala Tyr Ala Thr Glu Pro His Ala Lys Lys Lys Ser
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 18

Ala Thr Glu Pro His Ala Lys Lys Lys Ser
1               5                   10
```

METHODS FOR TREATING CARDIAC DISEASE BY MODIFYING AN N-TERMINAL DOMAIN OF TROPONIN I

This application is a divisional of U.S. patent application Ser. No. 11/311,472, filed on Dec. 19, 2005 now abandoned, which claims priority to U.S. Patent Application No. 60/638,073, filed on Dec. 20, 2004.

FIELD

The invention relates to the field of medicine. More particularly, the invention relates to cardiovascular health.

BACKGROUND

Cardiac muscle contraction is powered by actomyosin ATPase that is regulated by $Ca^{2+}$ binding to the troponin complex (references 1, 2, see below). A cardiac muscle cell contains multiple myofibrils that are composed of repeating contractile units called sarcomeres. A sarcomere is made up of partially overlapping assemblies of myosin filaments (the thick filaments) and actin filaments (the thin filaments) (Cooke, 1986; Leavis & Gergely, 1984; reviews). Actin-activated myosin ATPase (i.e., the actomyosin ATPase powers muscle contraction in a process regulated by $Ca^{2+}$ binding to the thin filament-associated proteins, tropomyosin and the troponin complex (Gordon et al., 2000; review). The current model for striated muscle (i.e., cardiac and skeletal muscle) contraction has contraction initiated by a rise in the cytoplasmic $[Ca^{2+}]$, which results in binding of $Ca^{2+}$ to troponin C (TnC). $Ca^{2+}$-TnC binding induces a series of allosteric changes in TnC, TnI, TnT and tropomyosin. These conformational changes allow the myosin head to form a strong cross-bridge with the actin filament. This interaction activates the myosin ATPase, displacing the thin filaments relative to the thick filaments and thus leading to a shortening of the sarcomere and contraction of the muscle (Cooke, 1986). TnI is the inhibitory subunit of troponin and plays a critical role in this $Ca^{2+}$-signaling system (Perry, 1999; review).

The troponin complex consists of three subunits: troponin C (TnC, the $Ca^{2+}$-binding subunit), troponin T (TnT, the tropomyosin-binding subunit), and troponin I (TnI, the inhibitory subunit) (2, 3). In addition to the core structure conserved in all TnI isoforms, cardiac TnI (cTnI) has an approximately 30-amino-acid N-terminal extension that is not present in fast and slow skeletal muscle TnIs. This N-terminal extension does not contain binding sites for other thin filament proteins (3, 4), but contains serine residues 23 and 24 which are protein kinase A (PKA) substrates. With β-adrenergic stimulation, phosphorylation of these serine residues facilitates myocardial relaxation by decreasing the affinity of TnC for $Ca^{2+}$ (5, 6).

In a rat tail-suppression model simulating the effect of weightlessness on the cardiovascular system, an N-terminal truncated cTnI was found to be up-regulated in the heart after three to four weeks of simulated weightlessness (7). This truncated cTnI is produced by restricted proteolysis, which removes the N-terminal amino acids 1-30. The restricted cleavage of cTnI selectively deletes the cardiac-specific N-terminal extension, including the regulatory serine residues, but leaves the core structure intact (7).

Long-term exposure to a weightless environment results in decreased cardiac function (8-10). A number of cardiovascular adaptations to weightlessness in microgravity and simulated microgravity occur in response to redistribution of body fluids to the head and neck region (11-16). In long-term exposure to microgravity and simulated microgravity, this fluid redistribution results in increased renal discharge of $Na^+$ and water to reduce circulatory blood volume and central venous pressure. According to the Frank-Starling relationship, cardiac function decreases as a result of this decreased preload. It is, therefore, important to determine whether proteolytic removal of the cTnI N-terminal domain has a negative impact on myocardial contractility or whether it is a compensatory response to the decrease of cardiac preload.

Characterization of the post-translational mechanisms in myocardial adaptation to long-term exposure to microgravity will provide a better understanding of myocardial dysfunction in astronauts, as well as in bedridden patients in which similar cardiovascular changes occur (9). The N-terminally truncated cTnI is present in normal hearts of all species examined (7). Understanding the functional effect of this structural modification of cTnI may increase our knowledge of mechanisms regulating myocardial contraction.

Thus, a need continues to exist in the art for methods of increasing the ventricular relaxation of the heart, resulting in an increased chamber filling and blood flow in accordance with the Frank Starling mechanism, thereby addressing such cardiac diseases, disorders and conditions as cardiac failure. Such methods should produce few, if any, side effects to maximize their value as therapeutics for the treatment of circulatory system disorders, such as cardiac diseases and disorders in humans.

SUMMARY

The invention effectively provides modified forms of cardiac troponin I (cTnI) such as N-terminally truncated forms of cTnI, including human cardiac troponin I, useful in treating or preventing circulatory diseases, disorders, or conditions such as cardiac diseases, disorders, or conditions resulting from or affected by insufficient blood flow. In an aspect of the invention, the methods comprise administering an N-terminally truncated or modified form of cTnI to a patient in need, including a human, pet, domesticated livestock, exotic or zoo animals and any organism exhibiting a circulatory system having a heart. Preferred organisms are mammals, such as humans. Administration includes production in vivo, such as by expression of an encoding nucleic acid in a host cell of the patient or non-human animal to be treated or suspected of being at risk of needing treatment.

In addition to administering a therapeutic protein or polypeptide, or a polynucleotide encoding same, the invention comprehends methods of screening for modulators of a proteolytic cleavage that yields an N-terminally truncated cTnI in vivo and for modulators of phosphorylation of cTnI residues Ser23, Ser24, or both, of a cTnI amino acid sequence such as SEQ ID NO:2. The polynucleotides, proteins or polypeptides, and modulators are useful in treating such cardiac diseases as cardiac failure by increasing ventricular relaxation, increasing chamber filling, and increasing stroke volume of the heart, consistent with known principles governing the physiology of the circulatory system in general, and the heart in particular, such as the Frank-Starling principle.

In another aspect, the invention provides methods of producing cardiac troponin I polypeptides other than wild-type full-length cTnI polypeptides. In particular, these methods comprise introducing a nucleic acid encoding a cTnI polypeptide, such as an N-terminally truncated cTnI or a modified cTnI, into a host cell and incubating the host cell under conditions suitable for expression of the nucleic acid, thereby producing the polypeptide. Optionally, the expressed polypeptide is purified by separation from at least one component of the host cell culture in which it was initially expressed. In some embodiments, the host cells are native to a patient or non-human animal in need of treatment or at risk of developing a cardiac condition requiring treatment. Included within these embodiments are applications of the invention in which the nucleic acid encoding the N-terminally truncated or modified cTnI is introduced into the patient's or non-human animal's cells in vivo. In addition to recombinant methods, the invention comprehends synthetic methods of producing the truncated or modified cTnIs. Exemplary N-terminally truncated or modified cTnIs are described below.

Another aspect of the invention is drawn to a method for monitoring cardiac function, and/or response(s) to at least one stress or disease condition, comprising measuring the level of a cardiac troponin I polypeptide selected from the group consisting of N-terminally truncated cardiac troponin I, an N-terminal fragment of cardiac troponin I and a modified cardiac troponin I, in a patient. These measurements can be absolute measurements that are compared to known, e.g., industry-accepted, standards. Alternatively, the measurement can determine the relative proportion of cardiac troponin I that is truncated in a given organism. Further, the measurement of a cardiac troponin I polypeptide can be made using any technique known in the art and it can be performed on any suitable sample obtained from the patient, such as a blood sample or a myocardial biopsy. In one embodiment of the method, the measuring comprises contacting a sample from the patient with an antibody specifically recognizing the peptide consisting of the sequence set forth in SEQ ID NO:5 and determining the level of binding of the antibody to the sample. A preferred organism is a human patient. A modified cTnI is a cTnI that has been derivatized by covalent or non-covalent modification of the cTnI, or by truncation of cTnI. For example, a covalent modification is phosphorylation (e.g., phosphorylation of Ser23 and/or Ser24); a non-covalent modification is the binding of the cTnI, preferably at a cTnI binding site including at least one amino acid of amino acids 1-30 of SEQ ID NO:2 of human cTnI or an equivalent region of a non-human cTnI, by at least one exogenous molecule, small molecule, peptide, or the like. Other exemplary modified cTnIs are cTnI polypeptides in which Ser23 and/or Ser24 is/are replaced by another amino acid, preferably one of the nineteen other conventional amino acids. Also preferred as replacements for Ser23 and/or Ser24 are polar amino acids, such as negatively charged amino acids that would present a negatively charged side chain at physiological pH, much like phosphoserine residues. A preferred truncated cTnI is an N-terminally truncated human cTnI. Exemplary truncated forms of human cTnI exhibit the sequence set forth in SEQ ID NO:2, but lack an N-terminal sequence selected from the group consisting of amino acid residues 1-26 of SEQ ID NO:2, 1-27 of SEQ ID NO:2, or 1-30 of SEQ ID NO:2.

Another aspect of the invention provides a method for treating a cardiac disorder by increasing ventricular relaxation comprising administering a therapeutically effective amount of a protein selected from the group consisting of an N-terminally truncated cardiac troponin I and a modified cardiac troponin I. A closely related aspect of the invention is drawn to a method for treating a cardiac disorder by increasing ventricular relaxation comprising producing a therapeutically effective amount of an N-terminally truncated cardiac troponin I in a host cell of a patient or non-human animal in need of treatment. The invention further comprehends the administration of a polynucleotide encoding an N-terminally truncated cardiac troponin I. The production results from expression of the polynucleotide, or nucleic acid, encoding an N-terminally truncated cardiac troponin I in a host cell of an organism being treated.

Yet another aspect of the invention is drawn to a method of screening for a modulator of the N-terminal structure of cardiac troponin I (cTnI) comprising (a) incubating a full-length cardiac troponin I in the presence and absence of a candidate modulator; (b) assessing the N-terminal structure of the cardiac troponin I; and (c) identifying a candidate modulator as a modulator of N-terminal structure of cardiac troponin I when the N-terminal structure of cTnI in the absence of the modulator differs from the N-terminal structure of cTnI in the presence of the modulator. In a related aspect, the method of screening further comprises protein kinase A in the incubating step, wherein the modulator is identified as a modulator of cardiac troponin I phosphorylation Modulators contemplated by the invention include those compounds, including peptides, that effectively promote or effect the endogenous cleavage of full-length cTnI, yielding the N-terminal segment of cTnI and N-terminally truncated cTnI, or that mimic the effect of N-terminal cleavage of cTnI. A preferred modulator of the phosphorylation level of cTnI is an inhibitor of phosphorylation. In some embodiments, the measuring comprises determining the binding between the cardiac troponin I and a specific anti-cardiac troponin I antibody that exhibits differential binding to a non-phosphorylated cTnI and a phosphorylated cTnI. These embodiments provide the advantage of epitope screening in which conformation changes in the target protein, cTnI, induced by a candidate modulator are detected based on a detectable alteration in the binding of a specific anti-cTnI antibody.

A related aspect of the invention provides a method of screening for a modulator of cardiac troponin I (cTnI) activity comprising (a) incubating a full-length cardiac troponin I in the presence and absence of a candidate modulator; (b) assessing cardiac troponin I activity; and (c) identifying a candidate modulator as a modulator of cardiac troponin I activity when the activity of cTnI in the absence of the candidate modulator differs from the activity of cTnI in the presence of the candidate modulator. In some embodiments of the method, the assessing comprises determining the conformation of cTnI in the presence and absence of the candidate modulator. Also in some embodiments, the assessing involves determining the conformation of a region of cTnI other than the N-terminal region (amino acids 1-30 of SEQ ID NO:5 in the case of human cTnIs).

The principle of epitope screening is made clearer by, e.g., Wang et al., Biochem. 37:14519-14528 (1998) and Jin et al., Biochem. 40:2623-2631 (2001), each incorporated herein by reference in its entirety. These embodiments include the use of monoclonal and polyclonal antibodies as well as the use of a plurality of distinctly characterized antibodies. The embodiments also extend to use of any known antibody form or variant, such as antibody fragments, single-chain antibodies (including single-chain variable fragments, diabodies, and the like), chimeric antibodies, mixed antibodies, humanized antibodies, and the like, provided that the antibody form or variant retains the capacity to specifically bind cTnI in phosphorylated and/or unphosphorylated form or specifically bind cTnI in other modified and/or unmodified forms. In other embodiments of the method of screening for a modulator, the measuring comprises determining the binding between the cardiac troponin I and a specific anti-cardiac troponin I antibody that exhibits differential binding to a non-modified cTnI and a modified cTnI. Exemplary modifications of cTnI include any N-terminal truncation that eliminates at least one of Ser23 and Ser24 from the nascently expressed cTnI, an internal, but N-terminally disposed, deletion that eliminates at least one of Ser23 and Ser24, and an amino acid substitution(s) for at least one of Ser23 and Ser24, e.g., by Asp and/or Glu.

In a related aspect, the invention provides a method of screening for a modulator of cardiac troponin calcium ($Ca^{2+}$) binding affinity comprising (a) incubating a cardiomyocyte preparation comprising a cardiac troponin I comprising a serine residue selected from the group consisting of Ser23 of SEQ ID NO:2 and Ser24 of SEQ ID NO:2 in the presence and absence of a candidate modulator; (b) measuring the level of contraction of the preparation; and (c) identifying a candidate modulator as a modulator of cardiac troponin I when the level of contraction of the preparation in the absence of the modulator differs from the level of contraction of the preparation in the presence of the modulator. In some embodiments, the contraction of the preparation is measured by determining the level of $Ca^{2+}$-induced actomyosin ATPase activity, with a modulator being identified on the basis of a difference in the levels of $Ca^{2+}$-induced actomyosin ATPase activity in the presence and absence of the modulator.

In another aspect, the invention provides a method of treating a cardiac disorder by increasing ventricular relaxation comprising administering a therapeutically effective amount of a modulator as described above (e.g., an inhibitor) to a patient in need. Any dosage and administration schedule known in the art may be used and such determinations are routinely made by those of skill in the art considering well-known variables affecting the general health of a given organism, or affecting the cardiovascular health of that organism.

Another aspect of the invention is drawn to a method of screening for a modulator of cardiac troponin I proteolytic cleavage comprising (a) contacting cytoplasmic components of a cardiomyocyte and a cardiac troponin I comprising a serine residue selected from the group consisting of Ser23 of SEQ ID NO:2 and Ser24 of SEQ ID NO:2 in the presence and absence of a candidate modulator; (b) measuring the level of N-terminal truncation of the cardiac troponin I; and (c) identifying a candidate modulator as a modulator of cardiac troponin I proteolytic cleavage when the cleavage level of cTnI in the absence of the modulator differs from the cleavage level of cTnI in the presence of the modulator. The cytoplasmic components of a cardiomyocyte include a cardiomyocyte lysate, an intact cardiomyocyte, an intact cardiac muscle or a heart, with exposure of a cTnI to a cell, tissue, or organ being understood to involve ultimate, or effective, contact with the cytoplasmic components of cells. A preferred modulator of proteolytic cleavage increases the proteolytic cleavage of cTnI. Preferably, such modulators increase the cleavage of cTnI approximately between amino acid residues 26-27, 27-28, or 30-31 of SEQ ID NO:2, for man, or equivalent positions in the cTnI of other species, thereby removing the N-terminal domain of the cTnI holoprotein.

In a related aspect, the invention provides a method for treating a cardiac disorder by increasing ventricular relaxation comprising administering a therapeutically effective amount of the modulator of proteolytic cleavage described above to a patient in need.

In another aspect, the invention provides a pharmaceutical composition for monitoring or treating a cardiac disorder, including a cardiac disease or condition, comprising an agent selected from the group consisting of a modified cardiac troponin I, an N-terminally truncated cardiac troponin I and a modulator thereof, in a pharmaceutically acceptable carrier. Modulators suitable for use in the pharmaceutical composition include modulators of the proteolytic N-terminal cleavage of cTnI and modulators that affect the phosphorylation of cTnI, e.g., the phosphorylation of at least one of serine residues 23 and 24 of SEQ ID NO:2. In preferred embodiments, the cardiac disorder is cardiac failure.

Yet another aspect of the invention is a kit for monitoring or treating a cardiac disorder comprising an agent selected from the group consisting of a modified cardiac troponin I, an N-terminally truncated cardiac troponin I and a modulator thereof, and a protocol for the use thereof to monitor or treat the cardiac disorder. The modulators are any of the modulators described above in the context of addressing pharmaceutical compositions. The cardiac disorder is cardiac muscle failure, either global or local, in preferred embodiments. In some embodiments, the modulator is a polypeptide that is defined by its capacity to specifically bind to a peptide consisting of the sequence set forth in SEQ ID NO:5. The modulator polypeptide may bind to a variety of forms of cTnI, however.

In a related aspect, the invention provides kits for screening for the modulators described herein along with protocols describing any known method or assay for identifying such modulators. A preferred assay is an epitope screening assay in which a candidate modulator is initially identified based on its capacity to bind to a cTnI target protein or polypeptide, thereby altering the displayed epitopes recognized by one or more specific anti-cTnI antibodies or analogous binding molecules.

A related aspect of the invention provides a kit for screening for a modulator of a cardiac troponin I activity selected from the group consisting of cTnI phosphorylation, cTnI-mediated troponin $Ca^{2+}$ binding affinity and N-terminal cleavage of cTnI, comprising a protocol for assaying for the modulator and a cTnI holoprotein or an N-terminally truncated cTnI as described herein. Any assay known in the art may be used. A preferred assay is an epitope screening assay.

Numerous additional aspects and advantages of the invention will become apparent to those skilled in the art upon consideration of the following detailed description of the invention, which describes presently preferred embodiments thereof.

BRIEF DESCRIPTION OF THE DRAWING

FIG. 1. Construction of transgenic mice over-expressing cTnI-ND in the heart. (A) Structural outlines of the naturally occurring N-terminal cleavage sites (indicated by the arrowheads) in cTnI and PCR engineering of cDNA encoding mouse cTnI-$ND_{29-21}$, corresponding to an average size of the three cTnI-ND variants found in rat heart (7). The two PKA substrate serine residues ($Ser_{23}$ and $Ser_{24}$) and $Ala_{29}$ (the truncation site for transgenic cTnI-ND) are noted in the sequences. The regions binding TnC and TnT were deduced from the partial crystal structure of cardiac troponin (4). (B) Construction of cTnI-ND cDNA into the T7 RNA polymerase-based pAED4 expression vector and production of N-terminus truncated cTnI in *E. coli* detected by Western blot using TnI-1 monoclonal antibody. Rat heart muscle (7) was used as control. S/D, ribosome-binding site; Tϕ, transcription termination site. (C) Transgene construct for over-expression of cTnI-ND cDNA under the control of α-MHC gene promoter. SV40 PA, SV40 poly-A segment. Positions of the PCR primers used in transgenic mouse screening are indicated.

FIG. 2. Expression of cTnI-ND in the transgenic mouse heart. (A) Total protein extracts from cTnI-ND transgenic mouse heart and other tissues were analyzed together with WT control by 12% SDS-PAGE with acrylamide:bisacrylamide ratio of 29:1 and Western blot using the anti-TnI monoclonal antibody TnI-1. The results demonstrate a cardiac-specific expression of cTnI-ND. (B) Representative Western blots show the expression of cTnI-ND at intermediate (INT-cTnI-ND) and high (H-cTnI-ND) levels. Previous results showed that in rat cardiac muscle, 84% of cTnI-ND was the Class I and Class 2 fragments (FIG. 1A) (7) and the exogenous cTnI-ND proteins in the transgenic mouse hearts can be distinguished from endogenous cTnI-ND by their different gel mobility. (C) Western blots using monoclonal antibody CT3 (mAb CT3) showed that expression of cardiac TnT in cTnI-ND transgenic mouse hearts was not altered, as compared with the WT control. (D) Western blot using mAb TnI-1 on Triton X-100® washed cardiac myofibrils showed proportional incorporation of cTnI-ND into the myofilaments of transgenic mouse cardiac muscle. The presence of cTnI-ND did not affect the incorporation of cardiac TnT into the myofilaments as shown by the CT3 mAb blot. TG, transgenic.

Figure 3:
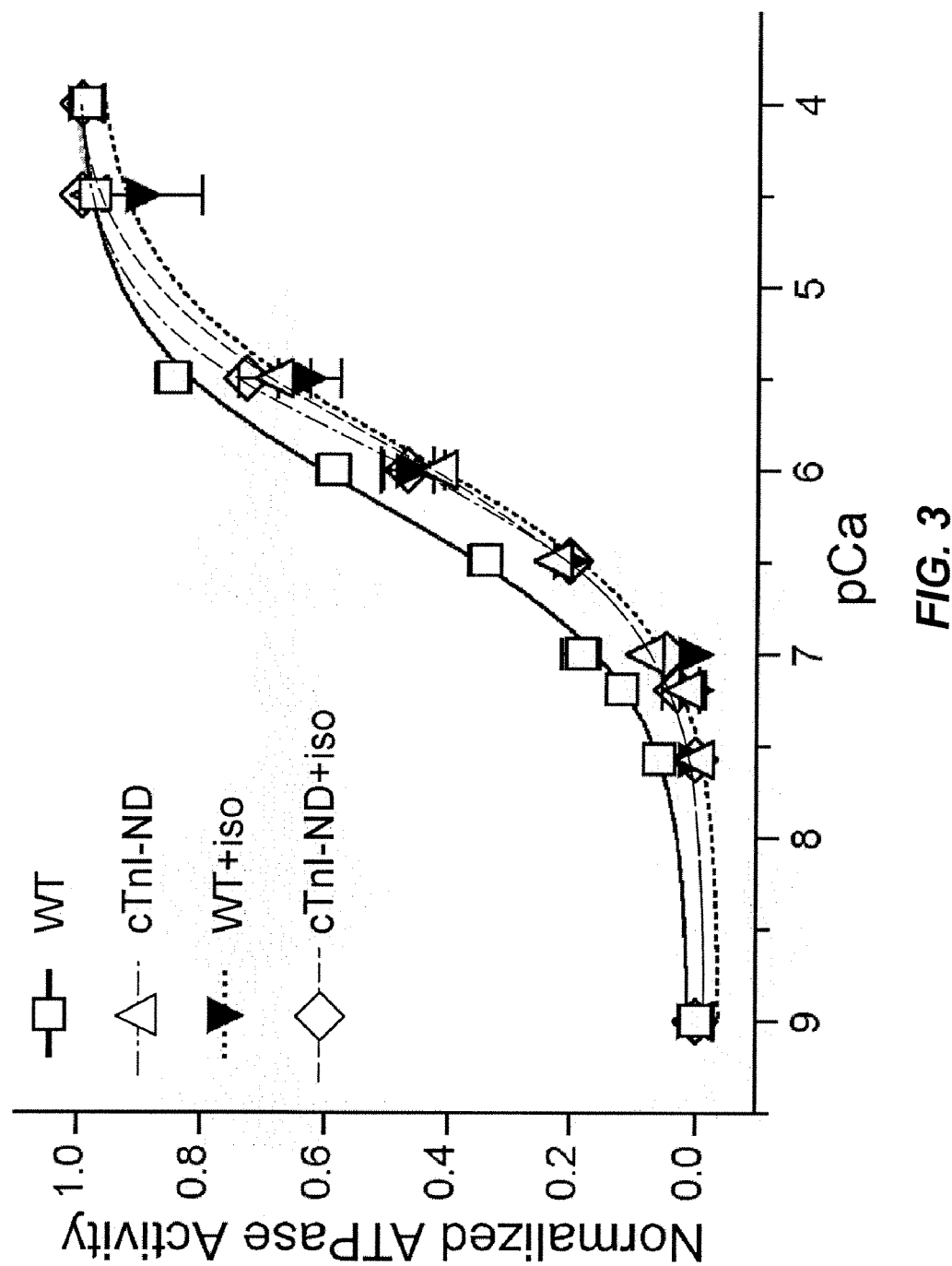

FIG. 3. Removal of the N-terminal domain of cTnI decreases the $Ca^{2+}$ sensitivity of actomyosin ATPase. Normalized $Ca^{2+}$-dependent actomyosin ATPase activation curves for isolated myofibrils were obtained from WT and H-cTnI-ND hearts with or without isoproterenol treatment. The results demonstrate that H-cTnI-ND myofibrils are less sensitive to $Ca^{2+}$ activation, similar to WT hearts upon β-adrenergic stimulation. In contrast, isoproterenol treatment did not produce any further decrease in $Ca^{2+}$ sensitivity in H-cTnI-ND myofibrils. The maximum ATPase rate was similar in cTnI-ND and WT mouse cardiac myofibrils (417±48 nmole Pi/mg protein/min and 422±73 nmole Pi/mg protein/min for the base line and 421±43 nmole Pi/mg protein/min and 418±57 nmole Pi/mg protein/min with isoproterenol treatment, respectively).

Figure 4:
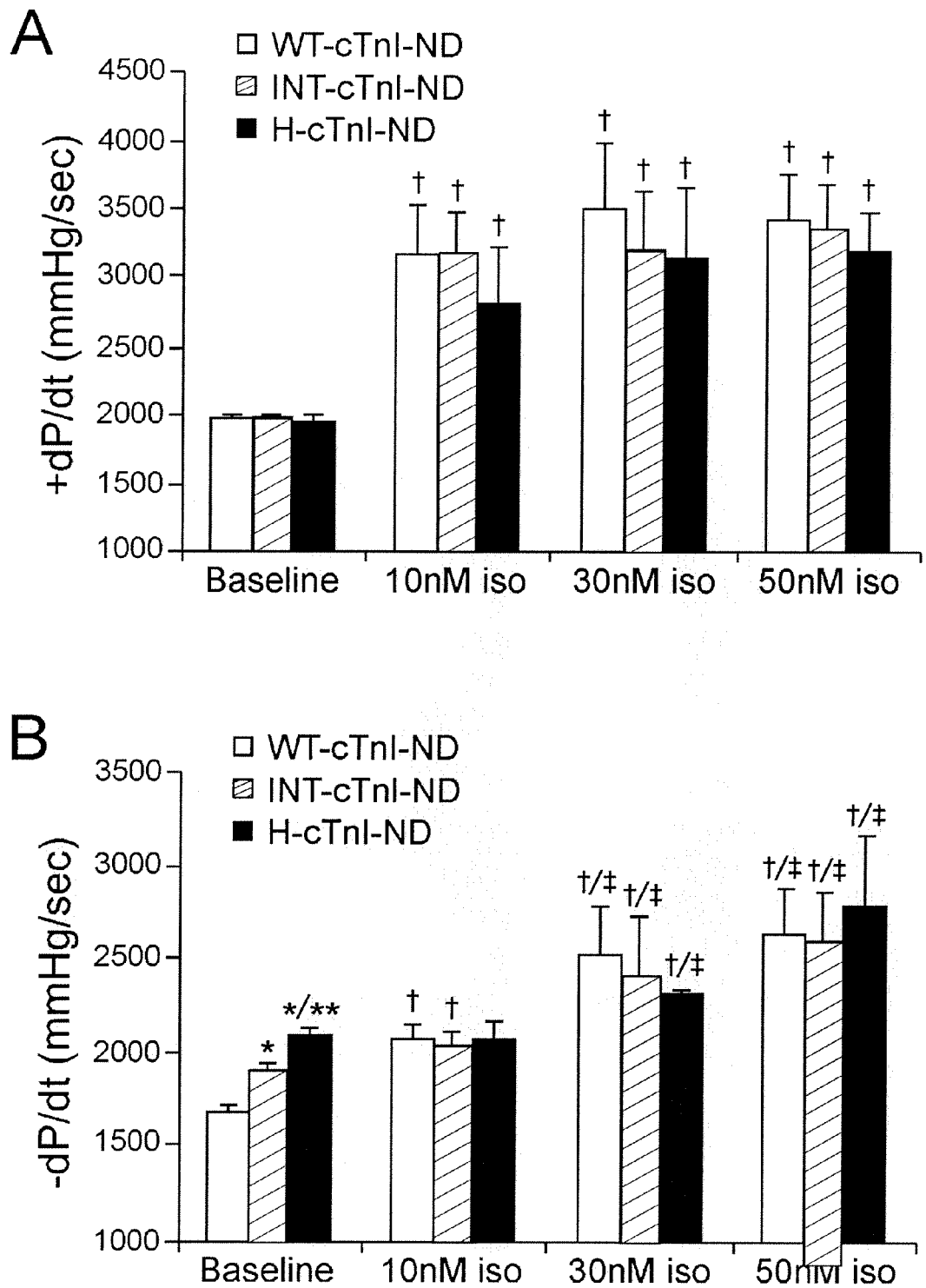

FIG. 4. Effects of isoproterenol treatment on the velocity of ventricular contraction and relaxation. Bar figures represent the average values for (A)+dP/dt and (B)-dP/dt measured from WT (n=16), INT-cTnI-ND (n=7) and H-cTnI-ND (n=11) mouse working hearts perfused with various concentrations of isoproterenol (iso). Data are shown as mean±SD. *Significantly different from WT baseline value (P<0.01); **Significantly different from INT-cTnI-ND baseline value (P<0.05); †Significantly different from baseline value of the same group (P<0.05); ‡Significantly different from 10 nM iso value of the same group (P<0.05).

Figure 5:
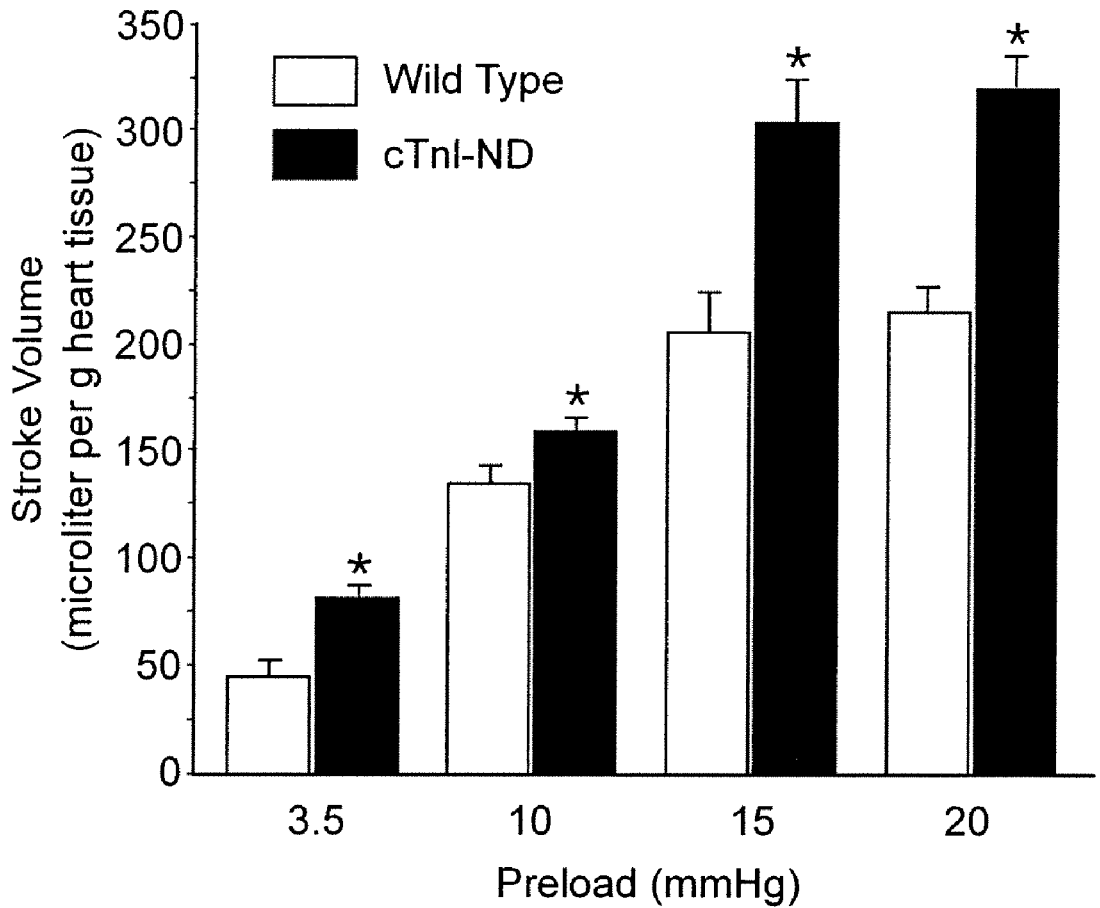

FIG. 5. Higher stroke volume of cTnI-ND hearts. Stroke volumes at 3.5, 10, and 20 mmHg preloads for WT (n=6) and H-cTnI-ND (n=6) hearts are shown as mean i SD. The results demonstrate that increases in preload produced increased stroke volume in both groups as expected from normal Frank-Starling relationship. However, compared with the WT controls, H-cTnI-ND hearts produced higher stroke volumes at all preloads tested.

Figure 6:
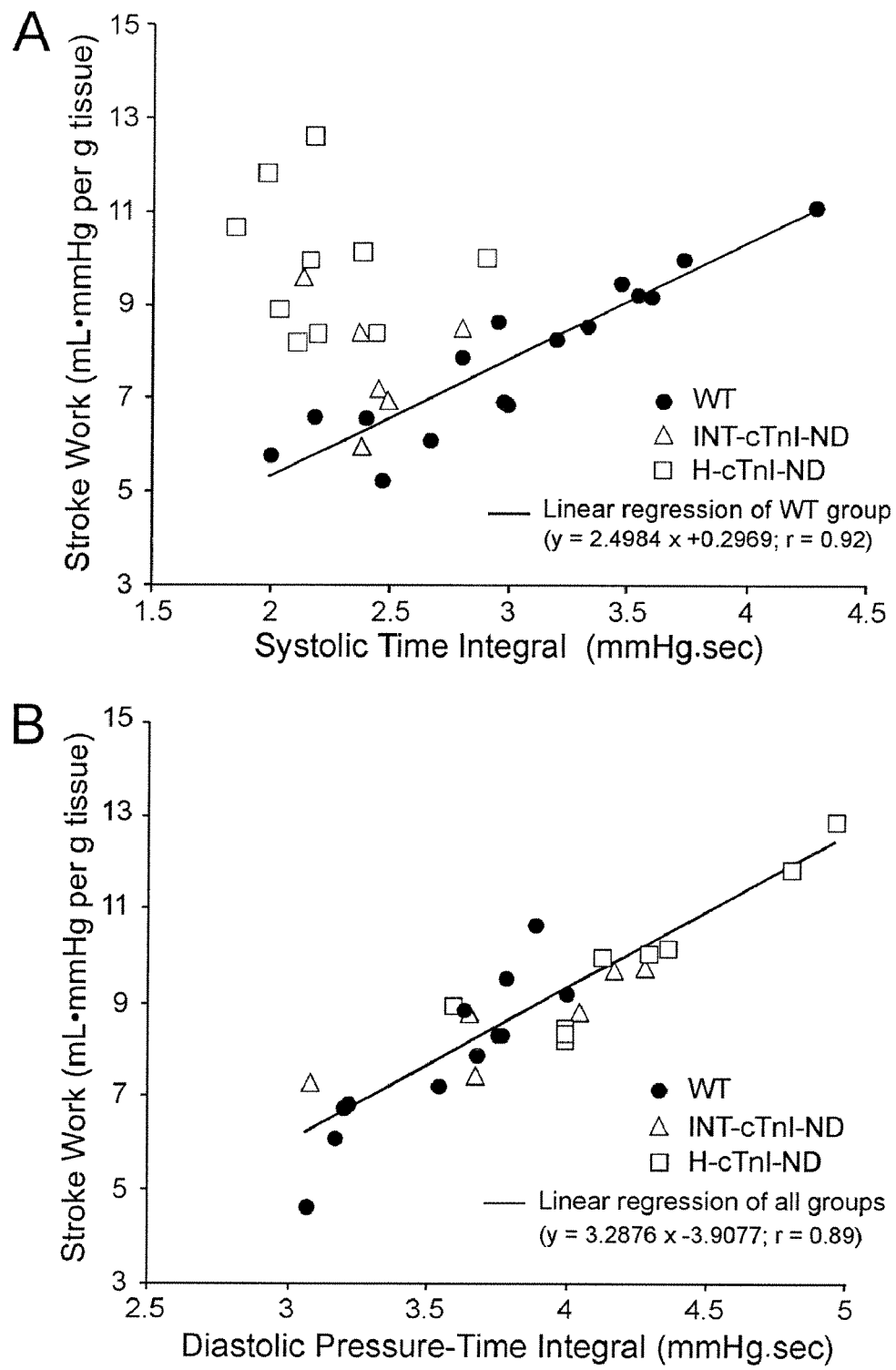

FIG. 6. Relationship between cardiac work and systolic and diastolic pressure-time integrals. The coordinates for WT, INT-cTnI-ND and H-cTnI-ND hearts are represented by solid diamonds, open triangles and open squares, respectively. (A) The solid line depicts the linear relationship between STI (systolic time integral) and stroke work for WT hearts (n=16). This relationship was diminished in the cTnI-ND hearts. (B) The solid line represents overall linear regression for DTI (diastolic time integral) and stroke work for all three groups. The assignment of independent and dependent variables in this figure was arbitrary and is not meant to imply a causative relationship.

Figure 7:
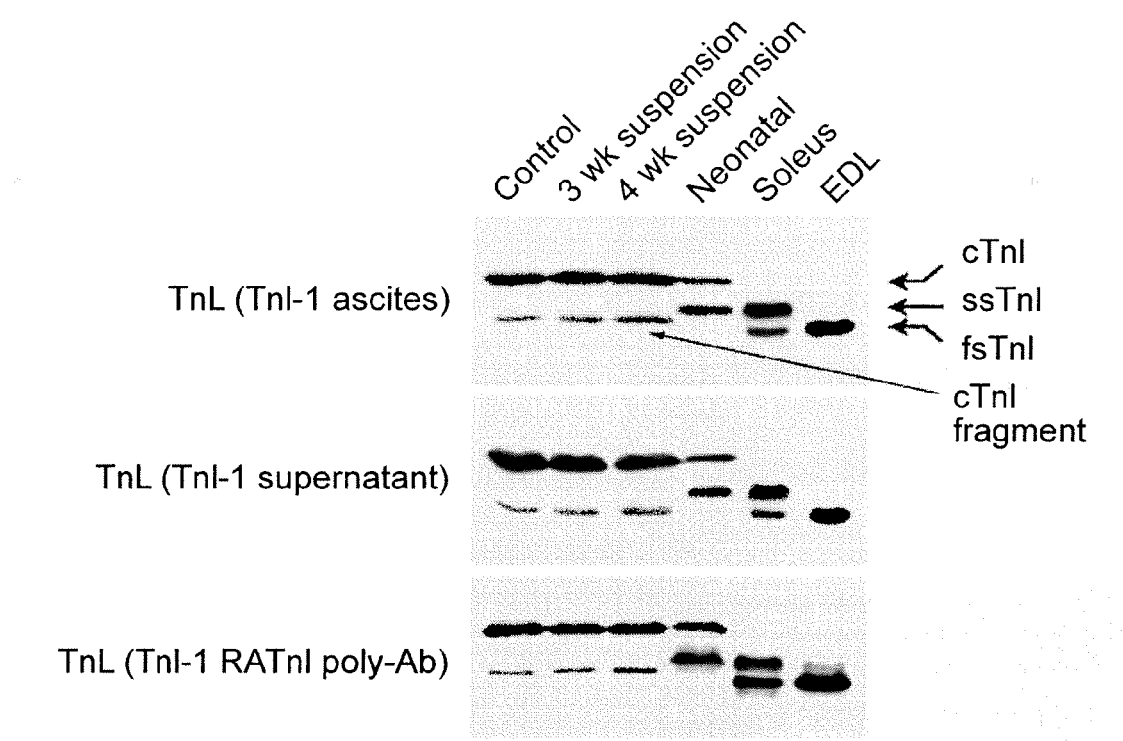

FIG. 7. Electrophoretic separation cardiac troponin I (cTnI), slow skeletal muscle troponin I (ssTnI), fast skeletal muscle troponin I (fsTnI), and a cardiac troponin I fragment (cTnI). The data show an increased level of cTnI fragment in the heart of tail-suspension rats.

Figure 8:
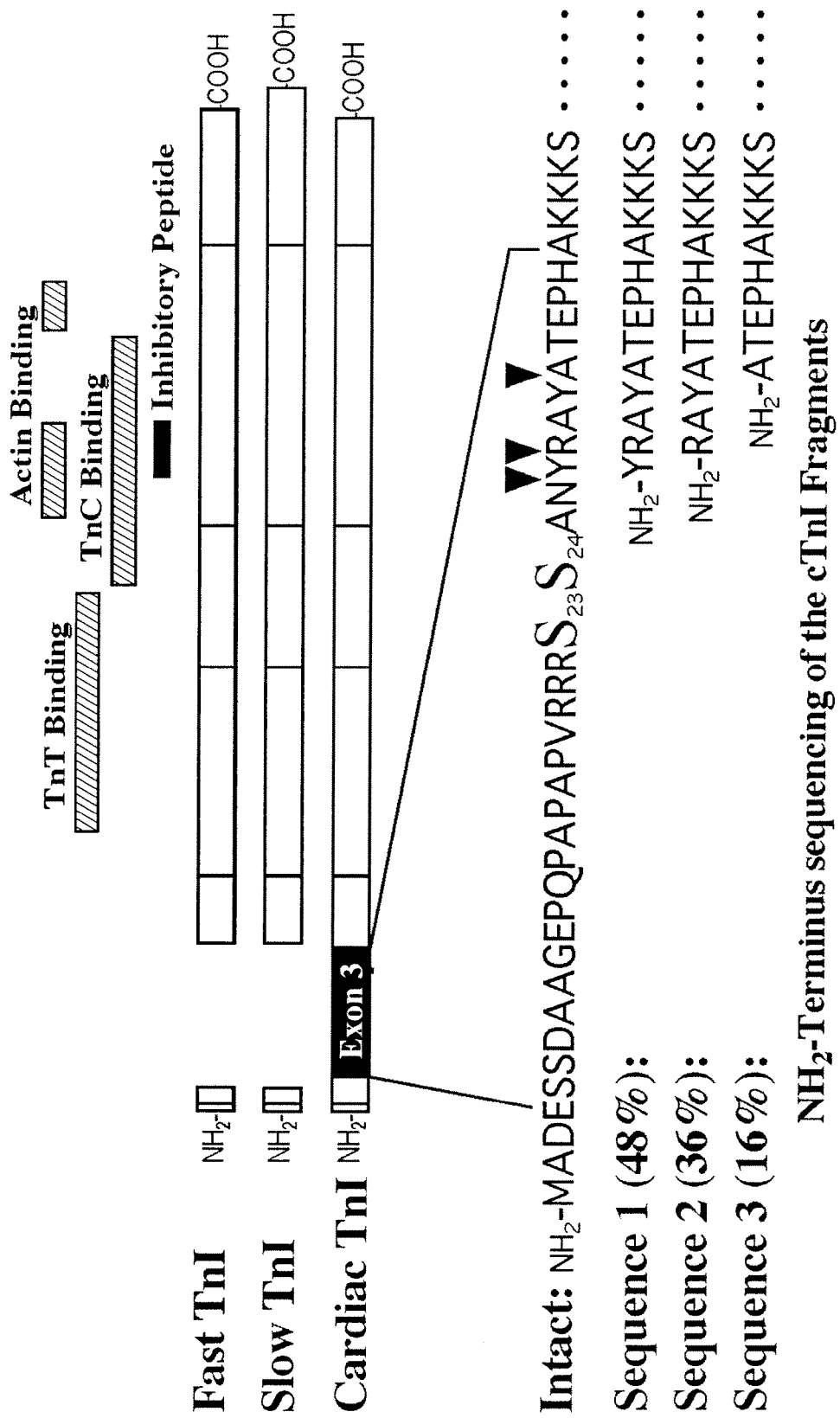

FIG. 8. A schematic illustration of the genetic organization of fast skeletal muscle, slow skeletal muscle and cardiac troponin I polypeptides, including N-terminal amino acid sequences and proteolytic cleavage sites.

Figure 9:
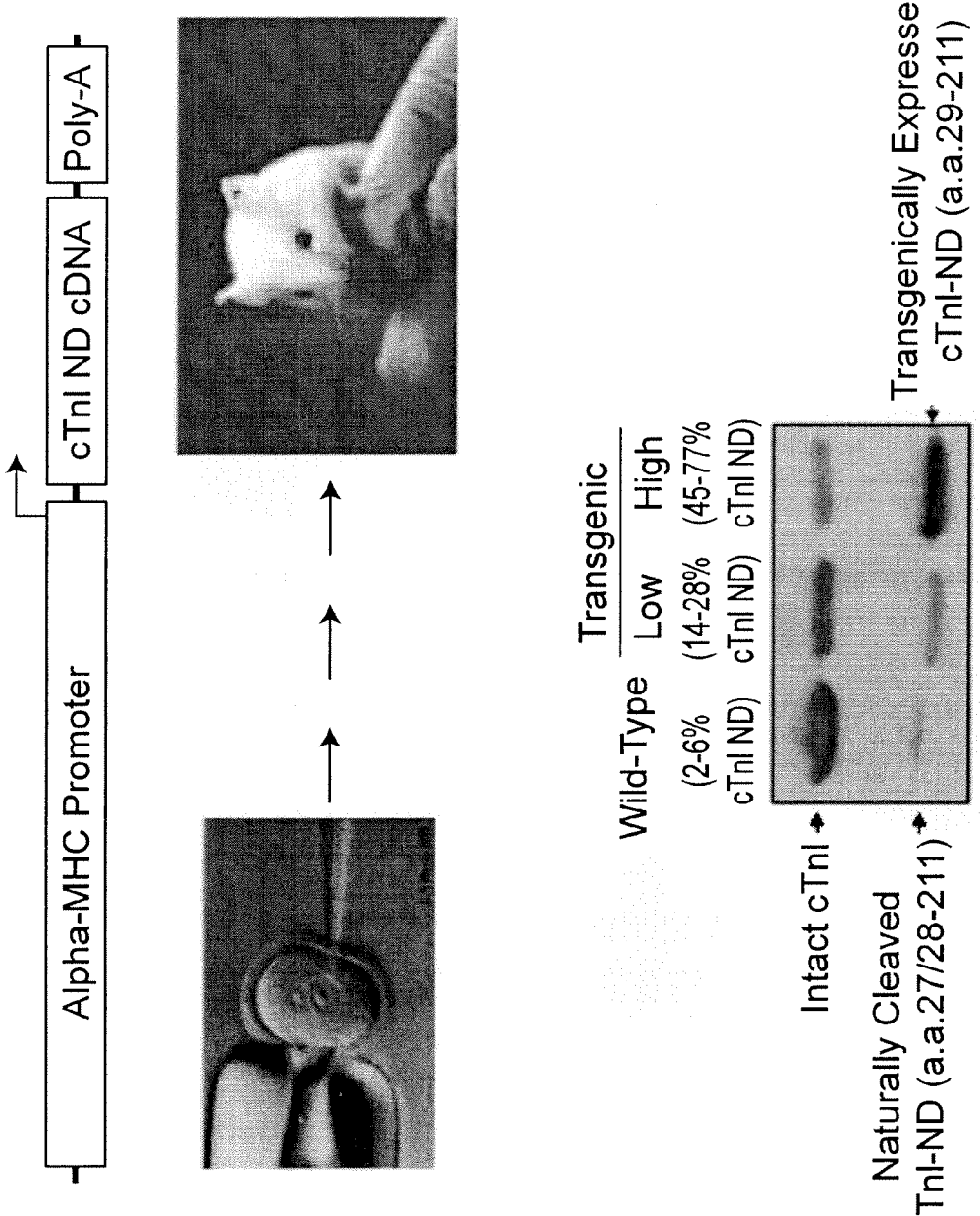

FIG. 9. Overexpression of N-terminally truncated cardiac troponin I in transgenic mice.

Figure 10:
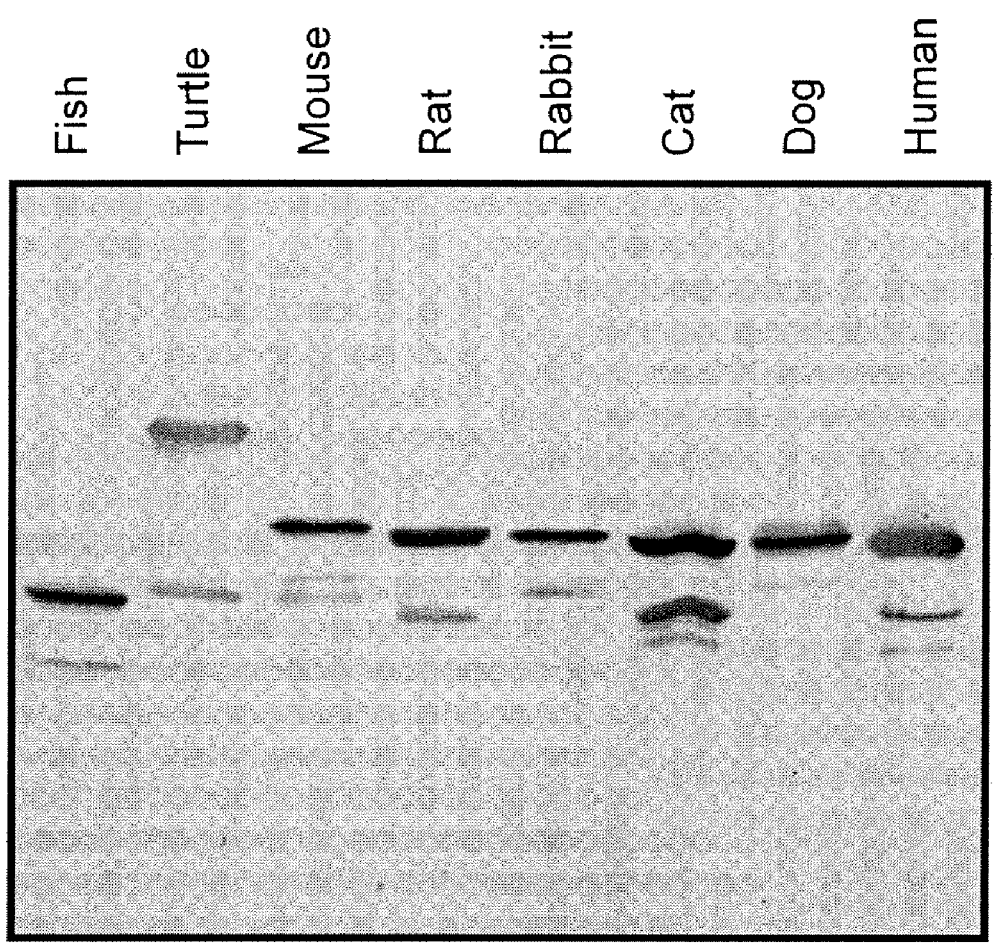

FIG. 10. Electrophoretogram illustrating the presence of cardiac troponin I fragments in the hearts of a wide variety of organisms, including fish, turtle and various mammals.

Figure 11:
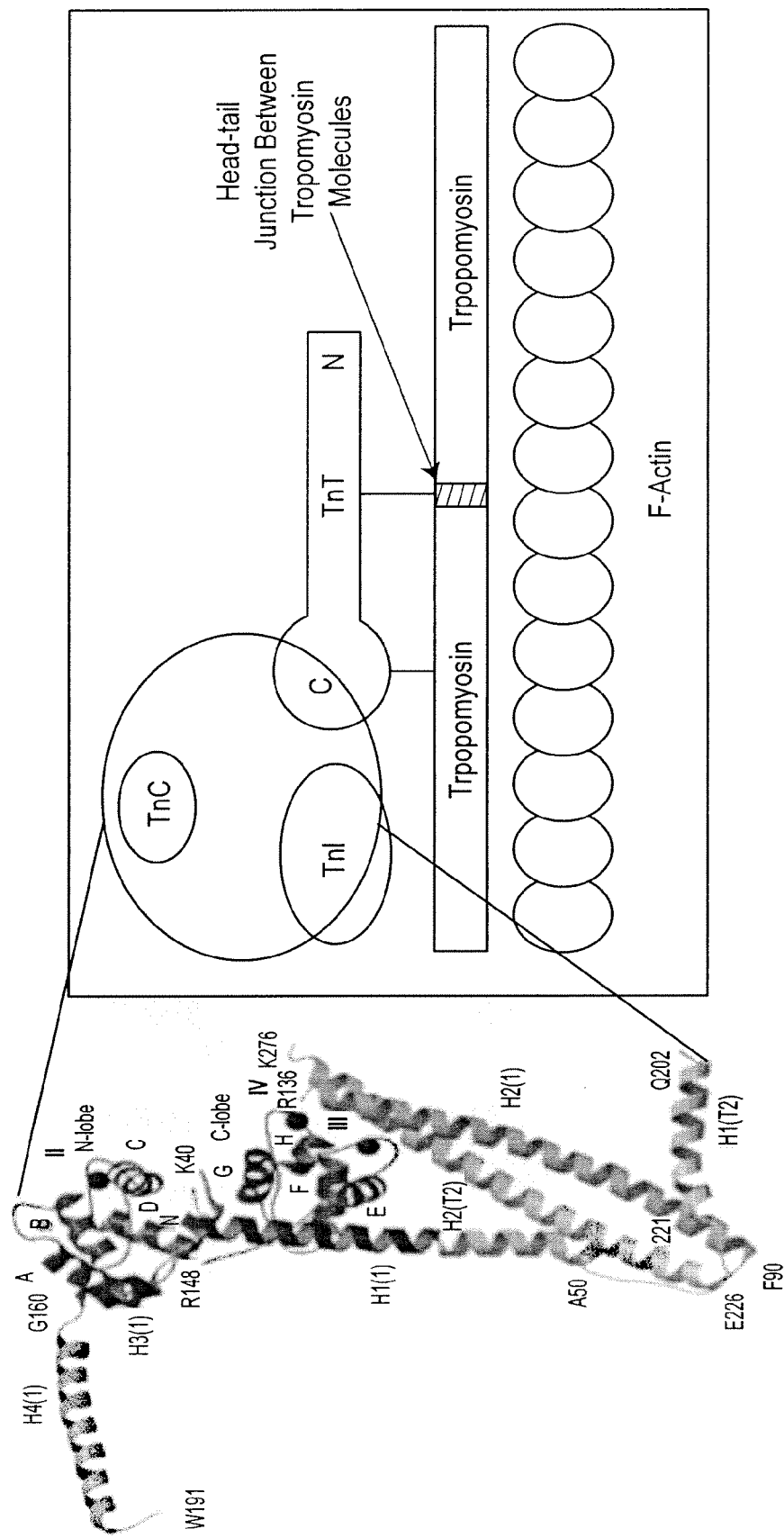

FIG. 11. Three-dimensional structure of cardiac troponin I and schematic illustration of the relationship of cTnI to other cardiac muscle proteins.

Figure 12:
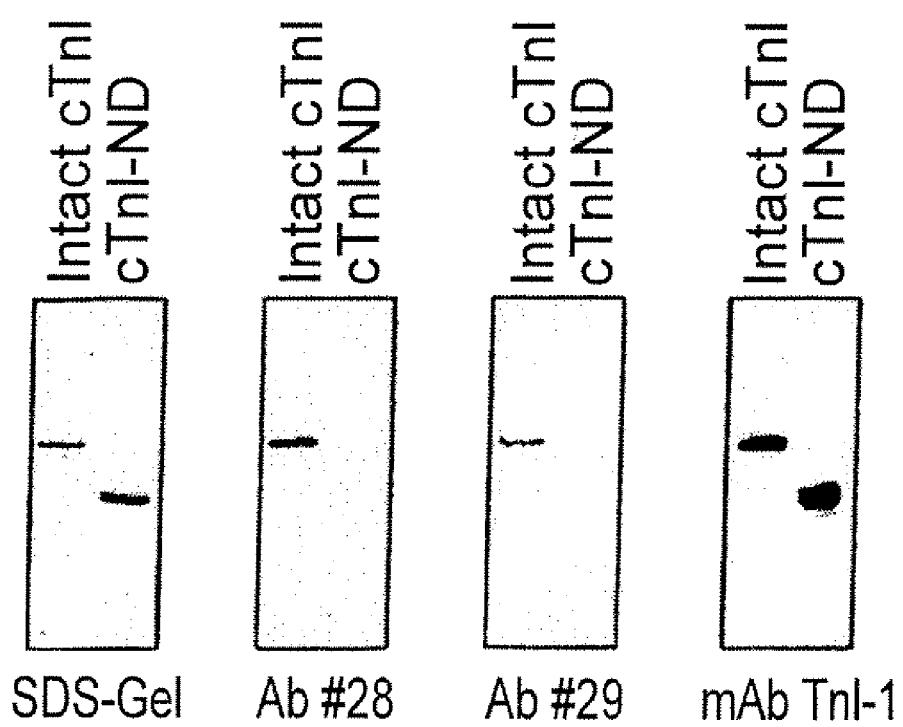

FIG. 12. Anti-cTnI N-terminal polyclonal antibodies. The Western blots show specific reaction of two anti-cTnI N-terminal peptide antibodies (#28 and #29) to intact cTnI with no cross-reaction to N-terminal truncated cTnI, confirming each of their specificities to the N-terminal peptide. A blot using an anti-TnI C-terminal monoclonal antibody is shown as a control.

Figure 13A:
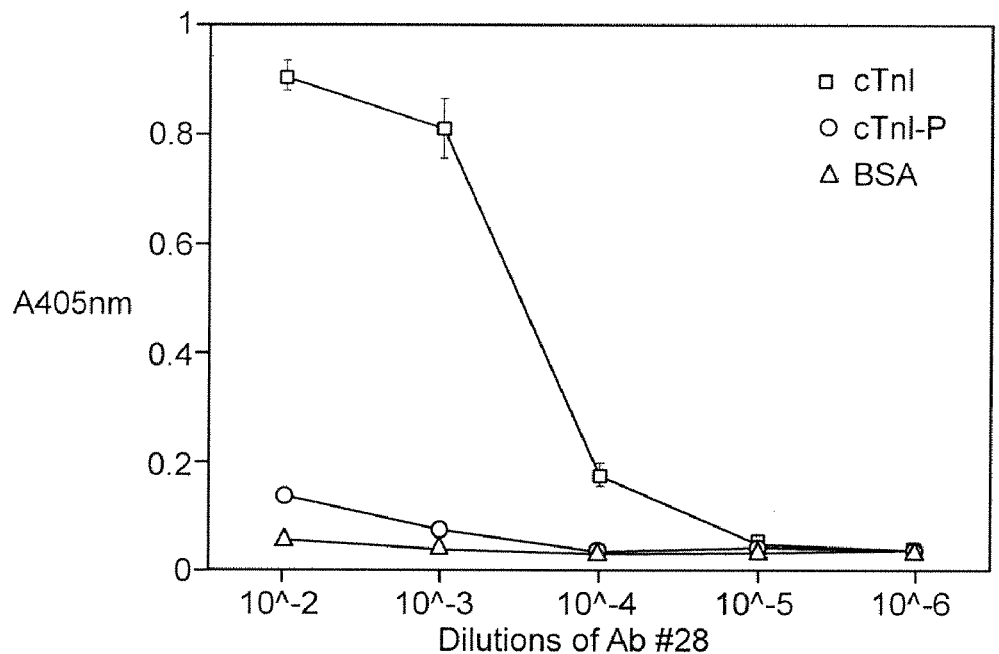
Figure 13B:
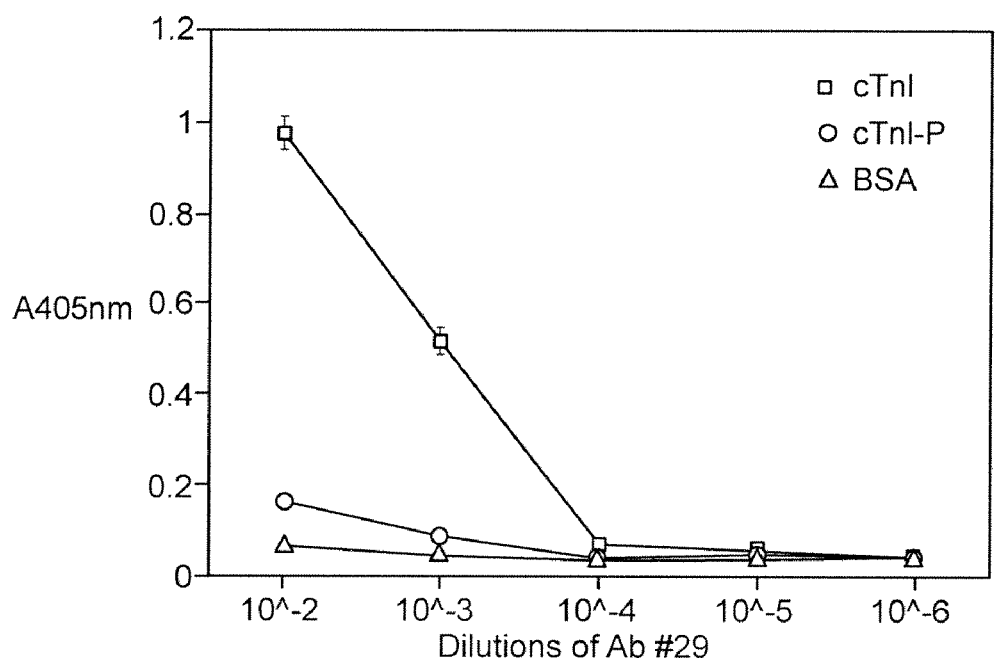

FIG. 13. ELISA detection of epitope conformational changes. ELISA titration curves were obtained using serial dilutions of two anti-cTnI N-terminal antibodies (AB #28 (FIG. 13A) and Ab #29 (FIG. 13B)) on non-phosphorylated and PKA-phosphorylated cTnI (cTnI-P) coated on microtiter plates. The results show significant decreases in the affinity of the anti-cTnI N-terminal antibodies resulting from PKA-catalyzed phosphorylation at Ser23/Ser24 in the N-terminal domain (FIG. 13A).

Figure 14:
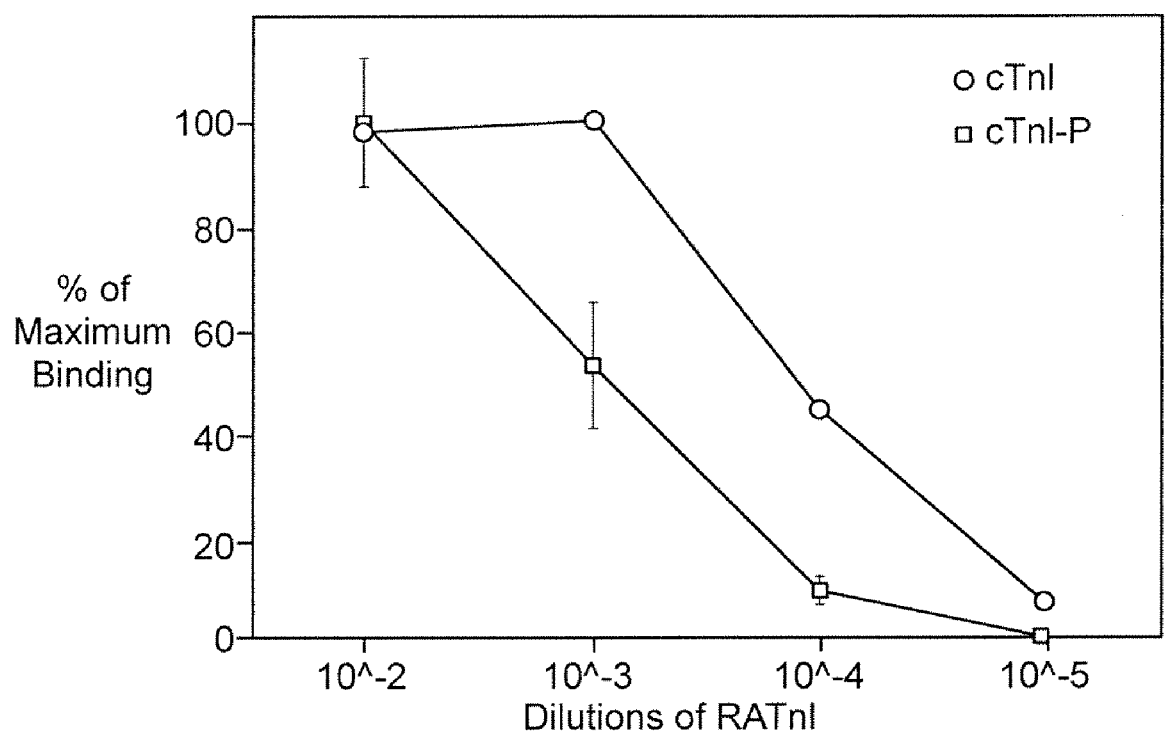

FIG. 14. N-terminal modification induced global conformational change in cTnI. ELISA titration curves were obtained using serial dilutions of a polyclonal anti-TnI antibody (RATnI) on non-phosphorylated and PKA-phosphorylated cTnI (cTnI-P) coated on microtiter plates. The results show that PKA-catalyzed phosphorylation produced significant decreases in the affinity of the RATnI polyclonal antibody raised against skeletal muscle TnI that lacks the cTnI N-terminal domain, reflecting changes in global molecular conformation. Bovine serum albumin was coated on the plates as the background control.

FIG. 15. Exemplary array design to scale-up ELISA screening for high-throughput formats. Each microtiter well in the 10×10 array contains a unique set of 10 of 100 molecules being subjected to assay. Each of the 100 molecules is uniquely identifiable by having a unique row and column identifier, but the format still allows for screening of 100 mixed samples. A positive molecule will result in one positive row and one positive column uniquely revealing its identity. For example, positive row J together with positive column IV indicates that molecule number 94 is positive.

Figure 16:
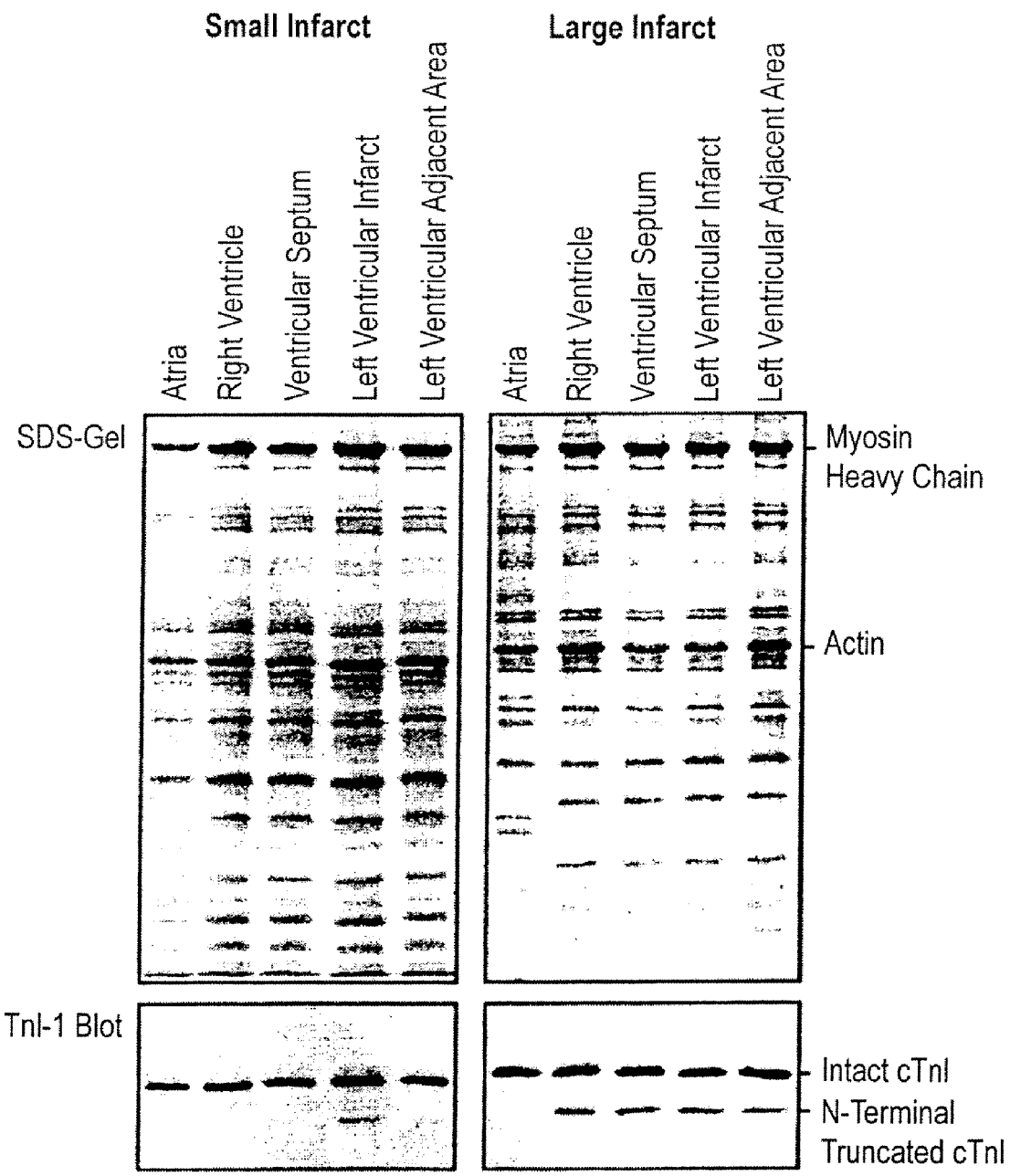

FIG. 16. SDS PAGE gels and Western blots using an anti-cTnI C-terminus monoclonal antibody, TnI-1, showing cardiac troponin I patterns in heart regions following ischemia treatment consistent with small or large infarcts.

DETAILED DESCRIPTION

To develop an integrated experimental system for characterizing the effect of removing the N-terminal extension of cTnI on cardiac function, we developed transgenic mice with postnatal over-expression of N-terminus truncated cTnI that lacks amino acids 1-28 (cTnI-ND) for biochemical and physiological characterization. cTnI-ND cardiac myofibrils showed a lower affinity for $Ca^{2+}$ than controls in actomyosin ATPase assay, similar to the effect of isoproterenol treatment. cTnI-ND hearts had a significantly faster rate of relaxation and lower left ventricular end diastolic pressure (LVEDP) compared to controls. The higher baseline relaxation rate of cTnI-ND hearts was similar to that of wild type (WT) mouse hearts under β-adrenergic stimulation. The decrease in cardiac output due to lowered preload was significantly smaller for cTnI-ND hearts compared to controls. These findings indicate that removal of the N-terminal extension of cTnI via restricted proteolysis enhances cardiac function by increasing the rate of myocardial relaxation and lowering LVEDP, in order to facilitate ventricular filling for a better utilization of the Frank-Starling mechanism.

Besides the core structure conserved in all troponin I isoforms, cardiac troponin I (cTnI) has an N-terminal extension that contains phosphorylation sites for protein kinase A under β-adrenergic regulation (see FIG. 11 for three-dimensional structure and schematic relationships to other cardiac muscle proteins). A restricted cleavage of this N-terminal regulatory domain occurs in normal cardiac muscle and is up-regulated during hemodynamic adaptation (Yu et al., *J. Biol. Chem.* 276, 15753-60, 2001). Transgenic mice were developed that over-express the N-terminally truncated cTnI (cTnI-ND) (see FIG. 9) in the heart to examine its biochemical and physiological significance. $Ca^{2+}$-activated actomyosin ATPase activity showed that cTnI-ND myofibrils had lower affinity for $Ca^{2+}$ than controls, similar to the effect of isoproterenol treatment. In vivo and isolated working heart experiments revealed that cTnI-ND hearts had a significantly faster rate of relaxation and lower left ventricular end diastolic pressure (LVEDP) compared to controls. The higher baseline relaxation rate of cTnI-ND hearts was at a level similar to that of wild-type mouse hearts under β-adrenergic stimulation. The decrease in cardiac output due to lowered preload was significantly smaller for cTnI-ND hearts compared to controls. These findings indicate that removal of the N-terminal extension of cTnI via restricted proteolysis enhances cardiac function by increasing the rate of myocardial relaxation and lowering LVEDP to facilitate ventricular filling, thus resulting in better utilization of the Frank-Starling mechanism. Administering such truncated molecules, or administering agents (e.g., phosphorylation and/or cleavage modulators), will mimic this effect and provide the medical and veterinary communities with a powerful tool for monitoring and treating circulatory diseases, disorders, and conditions, as well as open up avenues for developing second-generation diagnostics and therapeutics by making available assays for modulators of relevant cTnI modifications (e.g., cleavage and/or phosphorylation). It is understood that over-expressing a polynucleotide or nucleic acid encoding a truncated cTnI provides another approach to administering a truncated cTnI and such approaches are within the scope of the invention.

In addition to modification of cTnI by N-terminal truncation, other modifications also provide beneficial effects on cardiac function. As used herein, a modified cTnI is a cTnI that has been derivatized by covalent or non-covalent modification of the cTnI, or that is truncated relative to the full-length wild-type cTnI nascently expressed in vivo. For example, a covalent modification is phosphorylation (e.g., phosphorylation of Ser23 and/or Ser24) or other chemical modification due to administration of a compound (e.g., alkylation via an alkylating agent known in the art); a non-covalent modification is the binding of the cTnI, preferably at a cTnI binding site including at least one amino acid of amino acids 1-30 of SEQ ID NO:2 of human cTnI or an equivalent region of a non-human cTnI, by at least one exogenous molecule, small molecule, peptide, or the like. Exemplary peptides are antibodies, including whole antibodies (polyclonal or monoclonal), antibody fragments such as scFvs and diabodies, chimeric antibodies, antibody fusions, humanized antibodies, and any other antibody form known in the art.

cTnI function is regulated by restricted proteolysis. Post-translational modification forms an important regulation of cTnI function. PKA-catalyzed phosphorylation of $Ser_{23}$ and $Ser_{24}$ in the N-terminal domain of cTnI has been extensively investigated for roles in the β-adrenergic response. While proteolytic degradation of cTnI at the C-terminus was found to result in myocardial dysfunction (46, 47), a physiological regulation of myocardial function by restricted cleavage of cTnI at the N-terminus is a novel hypothesis. Selectively removing the N-terminal extension of cTnI retains the conserved core structure of TnI (FIG. 1A) and thus would not disrupt the formation of the troponin complex as shown in previous in vitro studies (48). The disclosure reveals a role for cTnI-ND in modulating normal function of the heart, as well as during myocardial adaptation to stress conditions. Whereas contractile force and velocity was reduced in cardiac muscle of tail suspension rats (7), it was unclear whether the decrease in contractility was caused by removal of the N-terminal domain of cTnI or the up-regulation of cTnI-ND was a result of the decrease, i.e. compensatory adaptation. To test the hypothesis that the proteolytic N-terminal truncation of cTnI is an intrinsic post-translational mechanism to modulate thin filament based $Ca^{2+}$ regulation of cardiac muscle, this disclosure provides evidence that restricted deletion of the N-terminal extension of cTnI facilitates relaxation of cardiac muscle and enhances cardiac function.

The cTnI-ND transgenic mice provide an integrated experimental system to study myocardial function under physiological conditions. In addition to biochemical activity at the myofibrillar level and in vivo evaluation of cardiac function, the isolated working heart allows detailed measurements of ventricular function under various hemodynamic conditions and pharmacological stimulation without the complexities of systemic neurohumoral regulation (29-31). The apparently normal cardiac function of the transgenic mice, with up to 82% cTnI replaced by cTnI-ND, supports the hypothesis that the selective deletion of a cTnI N-terminal domain is not destructive. In fact, the data show that removal of the N-terminal extension of cTnI enhances myocardial relaxation, indicating a positive regulatory mechanism of cardiac function. Therefore, the increased levels of proteolytic removal of cTnI N-terminal domain during long-term exposure to simulated microgravity provides an adaptive mechanism to compensate for cardiac function when circulatory blood volume is reduced (7).

Increased myocardial relaxation provides a beneficial effect on heart function. Ventricular filling depends upon the venous return and the relaxation of the ventricular muscle. A logical consequence of the increased rate of myocardial relaxation and time available for ventricular filling (the abbreviated duration of systole and longer duration of diastole) is a larger end-diastolic volume with effect on the length-tension relationship of the ventricular muscle (37-39). An increase in ventricular relaxation will result in a lower end-diastolic pressure and more ventricular filling. Indeed, FIG. 5 shows cTnI-ND hearts produced higher output than the control. The ratio is significantly greater at 3.5 mmHg preload pressure versus the higher preload pressures. This finding suggests that cTnI-ND hearts have a greater ventricular relaxation compared to the wild-type (WT) hearts, which would allow for better utilization of the Frank-Starling mechanism. This Frank-Starling mechanism-based beneficial effect can be seen in FIG. 6B as the positive correlation between DTI and stroke work in cTnI-ND as well as in WT hearts, in which H-cTnI-ND heart data clustered at the higher end of the stroke work scales. By having a faster ventricular relaxation and longer diastolic duration, the cTnI-ND hearts allow for better filling of the ventricle, especially when central venous pressure (preload) is lowered. This observation indicates that cTnI N-terminal truncation is an attractive mechanism to improve heart function by enhancing the diastolic function of cardiac muscle.

The preload and afterload in vivo depend on the characteristics of both the heart and the vascular system. Guyton and colleagues developed the concept that the control of cardiac output in vivo is a complex interplay of cardiac function and vascular function (50). The cardiac output varies directly with central venous pressure whereas the central venous pressure varies inversely with cardiac output. Although in vivo cardiac output was not measured in the present study, an increase in cardiac output in the working heart experiments supports the hypothesis that the reduced LVEDP of cTnI-ND mice (Table 1) results in better filling of the ventricle and increased cardiac output in vivo.

TABLE 1

In vivo measurements of cardiac function

|  | WT (n = 6) | H-cTnI-ND (n = 6) |
|---|---|---|
| Heart rate (beats per min) | 549 ± 11 | 554 ± 12 |
| LVP (mmHg) | 116.4 ± 3 | 101.2 ± 2 * |
| LVEDP (mmHg) | 5.88 ± 1.7 | 1.61 ± 0.51 * |
| +dP/dt (mmHg · sec$^{-1}$) | 4899 ± 835 | 5321 ± 344 |
| −dP/dt (mmHg · sec$^{-1}$) | 3387 ± 544 | 5283 ± 250 * |

The data are shown as mean ± SD.
* Significantly different from the WT values (P < 0.01).
LVP, left ventricular pressure; LVEDP, left ventricular end diastolic pressure.

The data shows that STI values correlate positively with stroke work in control mouse hearts (FIG. 6A). In contrast, the significant deviation from this curve by H-cTnI-ND hearts suggests that transgenic mouse hearts can maintain outputs similar to WT hearts at a lower pressure generating expense mainly due to abbreviated systolic duration (Table 2). The INT-cTnI-ND group data are between that of WT and H-cTnI-ND groups, supporting a dose effect of N-terminal truncated cTnI.

duration of diastole, yielding deeper perfusion from the coronary arteries. Although overall coronary flows of the experimental groups were similar and proportional to heart weight-body weight ratios, the higher DTI/STI ratios of cTnI-ND hearts may also be beneficial in allowing better subendocardial perfusion.

Understanding the mechanism by which cTnI-ND increases the rate of cardiac muscle relaxation was advanced by finding that deletion of the N-terminal 30 amino acids of cTnI, or thereabouts, increased −dP/dt in transgenic mouse hearts in vivo (Table 1) and in isolated working preparations (Table 2). The increased velocity of relaxation provides the basis of increased duration of diastole (Table 2) and significantly decreased LVEDP (Table 1) to enhance cardiac function. The N-terminal region of cTnI contains the PKA phosphorylation sites, serine 23 and serine 24 (51). Upon β-adrenergic stimulation, PKA-catalyzed phosphorylation of these sites enhances relaxation by decreasing the affinity of TnC for $Ca^{2+}$ (52). Consistently, increased −dP/dt was found in response to 10 nM isoproterenol perfusion in WT mouse hearts. However, the same level of β-adrenergic stimulation did not produce an increase in −dP/dt in H-cTnI-ND hearts above the high baseline value (FIG. 4B). This unique phenomenon indicates that under baseline conditions, −dP/dt for H-cTnI-ND hearts may already be at the same level achieved in WT hearts as a result of moderate β-adrenergic stimulation.

In agreement with the increased rate of myocardial relaxation, myofibrils isolated from cTnI-ND hearts demonstrated decreased $Ca^{2+}$ sensitivity in actomyosin ATPase assays (FIG. 3). Consistent with previous studies (52), WT cardiac myofibrils showed a decrease in $Ca^{2+}$ sensitivity upon isoproterenol treatment. However, cTnI-ND myofibrils did not show such a response. Thus, restricted proteolytic N-terminal truncation of cTnI may have similar effects on cardiac muscle relaxation as that produced by phosphorylation of serines 23 and 24 on cTnI during β-adrenergic stimulation. Generally, the in vitro methods of the invention, such as the in vitro assays, are conducted in accordance with any number of

TABLE 2

Hemodynamic parameters of isolated working hearts

|  | WT (n = 16) | INT-cTnI-ND (n = 7) | H-cTnI-ND (n = 11) |
|---|---|---|---|
| Heart weight/Body weight (mg/g) | 4.30 ± 0.36 (×10$^{-3}$) | 4.26 ± 0.18 (×10$^{-3}$) | 4.24 ± 0.19 (×10$^{-3}$) |
| Heart Rate (beats per min) | 461 ± 13 | 469 ± 11 | 471 ± 5 |
| Stroke Volume (μL · g tissue$^{-1}$) | 134 ± 7.3 | 128 ± 8.5 | 159 ± 4.9* |
| +dP/dt (mmHg · sec$^{-1}$) | 1968 ± 204 | 1994 ± 243 | 1964 ± 200 |
| −dP/dt (mmHg · sec$^{-1}$) | 1686 ± 114 | 1930 ± 268* | 2102 ± 196*† |
| Duration of systole (ms) | 47.8 ± 1.79 | 43.0 ± 1.1* | 40.4 ± 1.14*† |
| Duration of diastole (ms) | 78.6 ± 1.52 | 83.33 ± 1.03 | 84.6 ± 1.95* |
| Time To Peak Pressure (ms) | 38.6 ± 2.88 | 37.3 ± 2.67 | 38.4 ± 1.74 |
| $RT_{10}$ (ms) | 9.9 ± 3.10 | 9.0 ± 0.77* | 7.11 ± 0.85*† |
| $RT_{50}$ (ms) | 33.6 ± 4.38 | 34.3 ± 2.51 | 29.8 ± 2.15*† |
| $RT_{80}$ (ms) | 52.1 ± 5.25 | 52.6 ± 3.09 | 47.3 ± 2.68*† |
| Systolic Pressure-Time Integral (STI; mmHg · sec) | 2.64 ± 0.112 | 2.43 ± 0.044* | 2.25 ± 0.045*† |
| Diastolic Pressure-Time Integral (DTI; mmHg · sec) | 3.45 ± 0.089 | 3.79 ± 0.080* | 4.11 ± 0.071*† |
| Stroke Work (mL · mmHg/g tissue) | 7.88 ± 1.67 | 7.76 ± 1.31 | 9.89 ± 1.49*† |

The measurements were done under a constant preload of 10 mmHg. The data are shown as mean ± SD.
*Different from the WT group (P < 0.01);
†Different from the INT-cTnI-ND group (P < 0.05).

Previous studies have established that the DTI/STI ratio correlates closely with the blood supply to the subendocardium (37-42). Because coronary perfusion occurs during diastole, a faster rate of relaxation would produce a longer well-known assays in the field of molecular biology and muscle cell physiology/biochemistry. In addition to the known use of isolated myofibrils, in vitro cultured myocytes are contemplated for use in the methods, with the in vitro cultured myocytes prepared according to known techniques (see, e.g., Metzger et al., J. Cell. Biol. 126:701-711 (1994), incorporated by reference herein in its entirety). Also contemplated are in vitro methods comprising manipulation of muscle cell lysates or extracts. In all of these embodiments of the methods, it is the ultimate contact with the cytoplasmic components of the muscle cell that is contemplated, and using such materials (i.e., isolated myofibrils, isolated sarcomeres and muscle cell lysates) in the methods disclosed herein is defined as being compatible with contacting the cytoplasmic components of the cells involved.

On the other hand, higher levels of isoproterenol perfusions (30 and 50 nM) produced significant increases in relaxation velocity in the cTnI-ND hearts to a level similar to that produced in the WT hearts (FIG. 4B). This result indicates that the β-adrenergic potential of cTnI-ND hearts is preserved and β-adrenergic stimulation remains effective through other dominant mechanisms, such as increased sarcoplasmic reticulum uptake of $Ca^{2+}$ via phospholamban phosphorylation (54).

Figure 2:
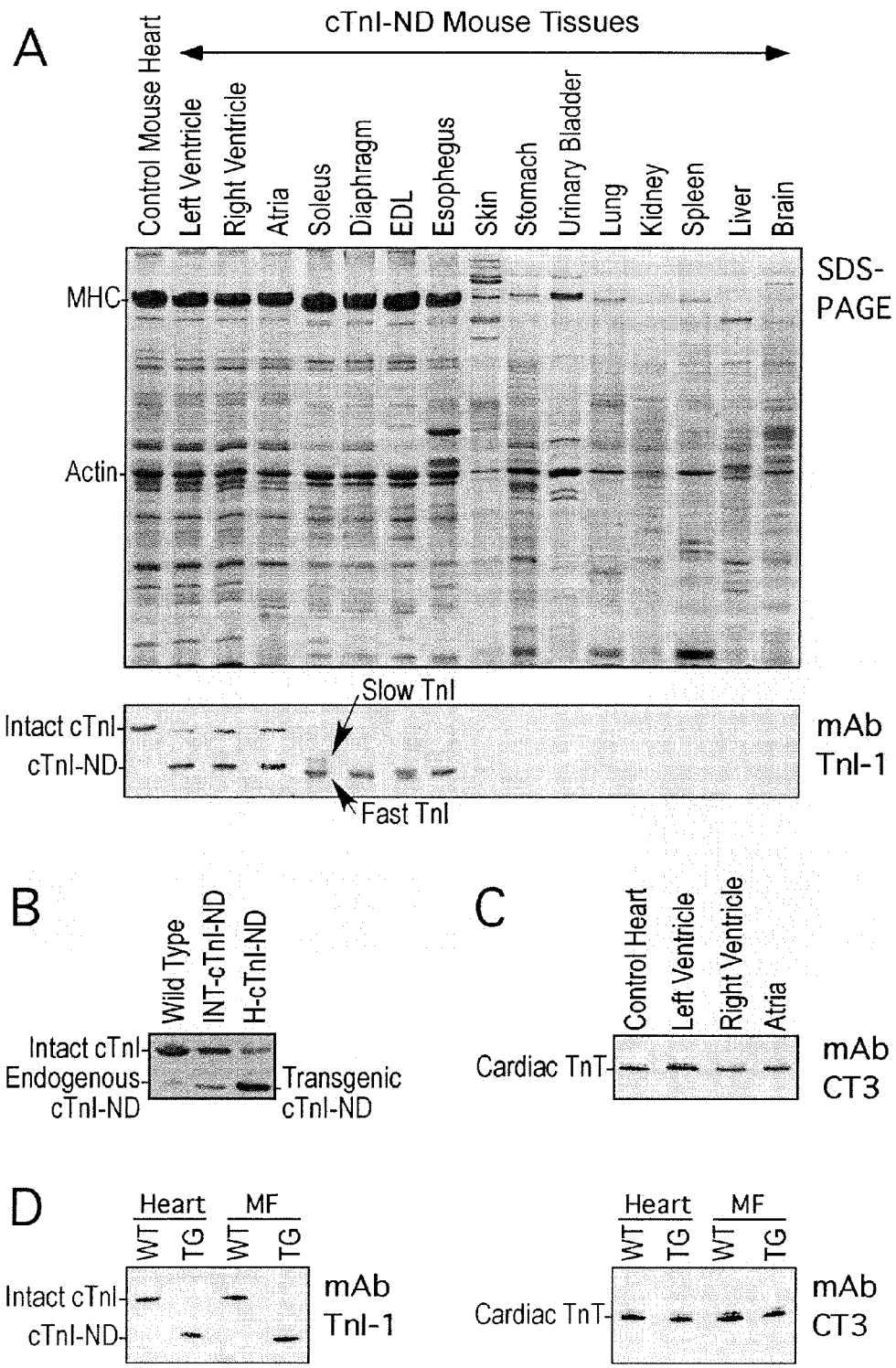

Quantitative differences between H-cTnI-ND and TNT-cTnI-ND hearts further suggest that the rate of relaxation is affected by the amount of cTnI-ND incorporated into the myofilaments (FIG. 2D). The dose-dependent effect is indicated by the findings that TNT-cTnI-ND hearts had relaxation rates, systolic durations, and STI and DTI values in between values of WT and H-cTnI-ND hearts. Although TNT-cTnI-ND hearts responded to β-adrenergic stimulation, the magnitude was smaller than observed in WT hearts. The quantitative effect for cTnI-ND to modulate cardiac muscle relaxation is suitable for a physiological regulatory mechanism during adaptation to functional demands.

Mammalian and avian embryonic cardiac muscles express slow skeletal muscle TnI that is replaced by cTnI during cardiac development (55, 56). This developmental switch of gene expression suggests that the N-terminal extension of cTnI, a structure absent from slow TnI (i.e., slow skeletal TnI), may play a unique role in the function of adult cardiac muscle. Similar to phosphorylation within this region, removal of the N-terminal domain from cTnI in adult heart facilitates relaxation provides new evidence for its role in regulating myocardial diastolic function. The diminished response in –dP/dt of cTnI-ND hearts to β-adrenergic stimulation is similar to that observed in transgenic mouse hearts over-expressing slow TnI that also lacks the PKA phosphorylation sites (45, 52). However, the opposite effects of cTnI-ND and slow TnI on the $Ca^{2+}$ sensitivity of cardiac muscle indicate functional differences due to the structural diversity in other regions of the TnI isoforms. For example, the functionally important C-terminal structure that is significantly different in cardiac and skeletal muscle TnI isoforms warrants further investigation.

It is worth noting that +dP/dt did not decrease in the cTnI-ND hearts. Therefore, myosin activity may be a dominant factor determining the maximum contractile velocity whereas the relaxation velocity is dependent on thin filament regulation. Since +dP/dt did not change but developed pressure was lower in the cTnI-ND heart in vivo (Table 1), these hearts might be working against a lower afterload. Therefore, secondary changes in the vascular system may also be present in the transgenic mouse model and contribute to the physiological effects of over-expressing N-terminally truncated cTnI.

The functional effects of cTnI-N-terminal truncation present a novel post-translational target for improving diastolic function of the heart. The increased β-adrenoreceptor responsiveness in simulated microgravity indicates a role of the β-adrenergic system during cardiovascular adaptation (49). However, β-adrenergic stimulation has a wide range of biological consequences that limit clinical application. In contrast, removal of the N-terminal domain of cTnI by restricted cleavage selectively utilizes a beneficial effect of the β-adrenergic system.

Generation of Antibodies

Polyclonal antibodies directed toward an antigen polypeptide generally are produced in animals (e.g., rabbits, hamsters, goats, sheep, horses, pigs, rats, gerbils, guinea pigs, mice, or any other suitable species) by means of multiple subcutaneous, intramuscular or intraperitoneal injections of antigen polypeptide, or a fragment thereof, and an adjuvant. Adjuvants include, but are not limited to, complete or incomplete Freund's adjuvant, mineral gels such as aluminum hydroxide, and surface-active substances such as lysolecithin, pluronic polyols, polyanions, peptides, oil emulsions, and dinitrophenol. BCG (bacillus Calmette-Guerin) and *Corynebacterium parvum* are also potentially useful adjuvants. It may be useful to conjugate an antigen polypeptide to a carrier protein that is immunogenic in the species to be immunized; typical carriers include keyhole limpet hemocyanin, serum albumin, bovine thyroglobulin, or soybean trypsin inhibitor. Also, aggregating agents such as alum are used to enhance the immune response. After immunization, the animals are bled and the serum is assayed for anti-antigen polypeptide antibody titer using conventional techniques. Polyclonal antibodies may be utilized in the sera from which they were detected, or may be purified from the sera using, e.g., Protein A, Protein G, or antigen affinity chromatography.

Monoclonal antibodies directed toward antigen polypeptides are produced using any method which provides for the production of antibody molecules by continuous cell lines in culture. For example, monoclonal antibodies may be made by the hybridoma method as described in Kohler et al., Nature 256:495 [1975]; the human B-cell hybridoma technique (Kosbor et al., Immunol Today 4:72, 1983; Cote et al., Proc Natl Acad Sci 80: 2026-2030, 1983) and the EBV-hybridoma technique (Cole et al., Monoclonal Antibodies and Cancer Therapy, Alan R Liss Inc, New York N.Y., pp 77-96, (1985). When the hybridoma technique is employed, myeloma cell lines may be used. Cell lines suited for use in hybridoma-producing fusion procedures preferably do not produce or do not secrete endogenous antibody, have high fusion efficiency, and exhibit enzyme deficiencies that render them incapable of growing in certain selective media which support the growth of only the desired fused cells (hybridomas). For example, where the immunized animal is a mouse, one may use P3-X63/Ag8, P3-X63-Ag8.653, NS1/1.Ag 41, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with cell fusions.

In an alternative embodiment, human antibodies can be produced from phage-display libraries (Hoogenboom et al., J. Mol. Biol. 227: 381 [1991]; Marks et al., J. Mol. Biol. 222: 581, see also U.S. Pat. No. 5,885,793). These processes mimic immune selection through the display of antibody repertoires on the surface of filamentous bacteriophage, and subsequent selection of phage by their binding to an antigen of choice. One such technique is described in PCT Application No. PCT/US98/17364, which describes the isolation of high affinity and functional agonistic antibodies for MPL- and msk-receptors using such an approach. In this approach, a complete repertoire of human antibody genes can be created by cloning naturally rearranged human V genes from peripheral blood lymphocytes as previously described (Mullinax, et al., Proc. Natl. Acad. Sci. (USA) 87: 8095-8099 [1990]).

Alternatively, an entirely synthetic human heavy chain repertoire can be created from unrearranged V gene segments by assembling each human $V_H$ segment with D segments of random nucleotides together with a human J segment (Hoogenboom, et al., J. Mol. Biol. 227:381-388 [1992]). Likewise, a light chain repertoire can be constructed by combining each human V segment with a J segment (Griffiths, et al, EMBO J. 13:3245-3260 [1994]). Nucleotides encoding the complete antibody (i.e., both heavy and light chains) are linked as a single chain Fv fragment and this polynucleotide is ligated to a nucleotide encoding a filamentous phage minor coat protein. When this fusion protein is expressed on the surface of the phage, a polynucleotide encoding a specific antibody can be identified by selection using an immobilized antigen.

Beyond the classic methods of generating polyclonal and monoclonal antibodies, any method for generating any known antibody form is contemplated. In addition to polyclonals and monoclonals, antibody forms comprehended by the invention include chimerized antibodies, humanized antibodies, CDR-grafted antibodies, and antibody fragments and variants.

Antibody variants and derivatives are also comprehended by the invention. Antibody variants having a variant sequence, i.e., a sequence that differs from a referent antibody sequence by the addition, deletion or substitution of at least one residue, provided that the antibody derivatives retain the capacity to specifically bind the common antigen (i.e., the antigen specifically bound by the referent antibody). In one example, insertion variants are provided wherein one or more amino acid residues supplement a specific binding agent amino acid sequence. Insertions may be located at either or both termini of the protein, or may be positioned within internal regions of the specific binding agent amino acid sequence. Variant products of the invention also include mature specific binding agent products, i.e., specific binding agent products wherein leader or signal sequences are removed, and the resulting protein having additional amino terminal residues. The additional amino terminal residues may be derived from another protein, or may include one or more residues that are not identifiable as being derived from a specific protein. Polypeptides with an additional methionine residue at position −1 are contemplated, as are polypeptides of the invention with additional methionine and lysine residues at positions-2 and -1 (Met-2-Lys-1-antibodies). Variants of the polypeptides of the invention having additional Met, Met-Lys, or Lys residues (or one or more basic residues in general) are particularly useful for enhanced recombinant protein production in bacterial host cells.

The invention also embraces specific polypeptides of the invention having additional amino acid residues which arise from use of specific expression systems. For example, use of commercially available vectors that express a desired polypeptide as part of a glutathione-S-transferase (GST) fusion product provides the desired polypeptide having an additional glycine residue at position-1 after cleavage of the GST component from the desired polypeptide. Variants which result from expression in other vector systems are also contemplated, including those wherein histidine tags are incorporated into the amino acid sequence, generally at the carboxy and/or amino terminus of the sequence.

In another aspect, the invention provides deletion variants wherein one or more amino acid residues in a polypeptide of the invention are removed. Deletions can be effected at one or both termini of the polypeptide, or from removal of one or more residues within the amino acid sequence. Deletion variants necessarily include all fragments of a polypeptide according to the invention.

Antibody fragments refer to polypeptides having a sequence corresponding to at least part of an immunoglobulin variable region sequence. Fragments may be generated, for example, by enzymatic or chemical cleavage of polypeptides corresponding to full-length antibodies. Other binding fragments include those generated by synthetic techniques or by recombinant DNA techniques, such as the expression of recombinant plasmids containing nucleic acid sequences encoding partial antibody variable regions. Preferred polypeptide fragments display immunological properties unique to, or specific for, a target as described herein. Fragments of the invention having the desired immunological properties can be prepared by any of the methods well known and routinely practiced in the art.

In still another aspect, the invention provides substitution variants of antibodies recognizing the N-terminal domain of cTnI (phosphorylated, unphosphorylated, or either form, the latter recognition being useful for antibodies used in comparative measures of cTnI forms and, thereby, the condition of cardiac muscle and cardiac function). Substitution variants include those polypeptides wherein one or more amino acid residues in an amino acid sequence are removed and replaced with alternative residues. In some embodiments, the substitutions are conservative in nature; however, the invention embraces substitutions that ore also non-conservative. Amino acids can be classified according to physical properties and contribution to secondary and tertiary protein structure. A conservative substitution is recognized in the art as a substitution of one amino acid for another amino acid that has similar properties. Exemplary conservative substitutions are set out in Table A (see WO 97/09433, page 10, published Mar. 13, 1997 (PCT/GB96/02197, filed Sep. 6, 1996), immediately below.

TABLE A

Conservative Substitutions I

| SIDE CHAIN | | CHARACTERISTIC AMINO ACID |
|---|---|---|
| Aliphatic | Non-polar | G A P I L V |
| | Polar - uncharged | S T M N Q |
| | Polar - charged | D E K R |
| | Aromatic | H F W Y |
| | Other | N Q D E |

Alternatively, conservative amino acids can be grouped as described in Lehninger, [Biochemistry, Second Edition; Worth Publishers, Inc. NY:NY (1975), pp. 71-77] as set out in Table B, immediately below.

TABLE B

Conservative Substitutions II

| SIDE CHAIN | CHARACTERISTIC AMINO ACID |
|---|---|
| | Non-polar (hydrophobic) |
| A. Aliphatic: | A L I V P |
| B. Aromatic: | F W |
| C. Sulfur-containing: | M |
| D. Borderline: | G |
| | Unchanged-polar |
| A. Hydroxyl: | S T Y |
| B. Amides: | N Q |

TABLE B-continued

Conservative Substitutions II

| SIDE CHAIN | CHARACTERISTIC AMINO ACID |
|---|---|
| C. Sulfhydryl: | C |
| D. Borderline: | G |
| Positively Charged (Basic): | K R H |
| Negatively Charged (Acidic): | D E |

The invention also provides derivatives of antibodies specifically recognizing at least one form of the N-terminal domain of cTnI. Derivatives include antibodies bearing modifications other than insertion, deletion, or substitution of amino acid residues. Preferably, the modifications are covalent in nature, and include for example, chemical bonding with polymers, lipids, other organic, and inorganic moieties. Derivatives of the invention may be prepared to increase the circulating half-life of a specific polypeptide, or may be designed to improve targeting capacity for the polypeptide to desired cells, tissues, or organs.

The invention further embraces antibodies that are covalently modified or derivatized to include one or more water-soluble polymer attachments, such as polyethylene glycol, polyoxyethylene glycol, or polypropylene glycol, as described U.S. Pat. Nos. 4,640,835, 4,496,689, 4,301,144, 4,670,417, 4,791,192 and 4,179,337. Still other useful polymers known in the art include monomethoxy-polyethylene glycol, dextran, cellulose, and other carbohydrate-based polymers, poly-(N-vinyl pyrrolidone)-polyethylene glycol, propylene glycol homopolymers, a polypropylene oxide/ethylene oxide co-polymer, polyoxyethylated polyols (e.g., glycerol) and polyvinyl alcohol, as well as mixtures of these polymers. Particularly preferred are polyethylene glycol (PEG)-derivatized proteins. Water-soluble polymers may be bonded at specific positions, for example at the amino terminus of the proteins and polypeptides according to the invention, or randomly attached to one or more side chains of the polypeptide. The use of PEG for improving therapeutic capacities is described in U.S. Pat. No. 6,133,426.

Certain strategies are available to manipulate the inherent properties of an antigen-specific antibody that are not available to non-antibody-based binding molecules. A good example of the strategies favoring antibody-based molecules over these alternatives is the in vivo modulation of the affinity of an antibody for its target through affinity maturation, which takes advantage of the somatic hypermutation of immunoglobulin genes to yield antibodies of increasing affinity as an immune response progresses. Additionally, recombinant technologies have been developed to alter the structure of immunoglobulins and immunoglobulin regions and domains. Thus, polypeptides derived from antibodies may be produced that exhibit altered affinity for a given antigen, and a number of purification protocols and monitoring screens are known in the art for identifying and purifying or isolating these polypeptides. Using these known techniques, polypeptides comprising antibody-derived binding domains can be obtained that exhibit decreased or increased affinity for an antigen. Strategies for generating the polypeptide variants exhibiting altered affinity include the use of site-specific or random mutagenesis of the DNA encoding the antibody to change the amino acids present in the protein, followed by a screening step designed to recover antibody variants that exhibit the desired change, e.g., increased or decreased affinity relative to the unmodified parent or referent antibody.

The amino acid residues most commonly targeted in mutagenic strategies to alter affinity are those in a complementarity-determining region (CDR) or hyper-variable region of the light and heavy chain variable regions of an antibody. These regions contain the residues that physicochemically interact with an antigen, as well as other amino acids that affect the spatial arrangement of these residues. However, amino acids in the framework regions of the variable domains outside the CDR regions have also been shown to make substantial contributions to the antigen-binding properties of an antibody, and can be targeted to manipulate such properties, as is known in the art. See Hudson, P. J. Curr. Opin. Biotech., 9: 395-402 (1999) and references therein.

Smaller and more effectively screened libraries of antibody variants can be produced by restricting random or site-directed mutagenesis to sites in the CDRs that correspond to areas prone to "hypermutation" during the somatic affinity maturation process. See Chowdhury, et al., Nature Biotech., 17: 568-572 (1999) and references therein. The types of DNA elements known to define hypermutation sites in this manner include direct and inverted repeats, certain consensus sequences, secondary structures, and palindromes. The consensus DNA sequences include the tetrabase sequence Purine-G-Pyrimidine-A/T (i.e., (A or G)-G-(C or T)-(A or T)) (SEQ ID NO:6) and the serine codon AGY (wherein Y can be C or T) (SEQ ID NO:7).

Thus, another aspect of the invention is a set of mutagenic strategies for modifying the affinity of an antibody for its target. These strategies include mutagenesis of the entire variable region of a heavy and/or light chain, mutagenesis of the CDR regions only, mutagenesis of the consensus hypermutation sites within the CDRs, mutagenesis of framework regions, or any combination of these approaches ("mutagenesis" in this context could be random or site-directed). Definitive delineation of the CDR regions and identification of residues comprising the binding site of an antibody can be accomplished through solving the structure of the antibody in question, and the antibody:ligand complex, through techniques known to those skilled in the art, such as X-ray crystallography. Various methods based on analysis and characterization of such antibody crystal structures are known to those of skill in the art and can be employed to approximate the CDR regions. Examples of such commonly used methods include the Kabat, Chothia, AbM and contact definitions.

The Kabat definition is based on sequence variability and is the most commonly used definition to predict CDR regions. Johnson, et al., Nucleic Acids Research, 28: 214-8 (2000). The Chothia definition is based on the location of the structural loop regions. See Chothia et al., J. Mol. Biol., 196: 901-17 (1986); Chothia et al., Nature, 342: 877-83 (1989). The AbM definition is a compromise between the Kabat and Chothia definitions. AbM is an integral suite of programs for antibody structure modeling produced by the Oxford Molecular Group (Martin, et al., Proc. Natl. Acad. Sci. (USA) 86:9268-9272 [1989]; Rees, et al., ABMTM, a computer program for modeling variable regions of antibodies, Oxford, UK; Oxford Molecular, Ltd.). The AbM suite models the tertiary structure of an antibody from primary sequence using a combination of knowledge databases and ab initio methods An additional definition, known as the contact definition, has been recently introduced. See MacCallum et al., J. Mol. Biol., 5:732-45 (1996). This definition is based on an analysis of the available complex crystal structures.

By convention, the CDR domains in the heavy chain are typically referred to as H1, H2 and H3, and are numbered sequentially in order moving from the amino terminus to the carboxy terminus. The CDR regions in the light chain are typically referred to as L1, L2 and L3, and are numbered sequentially in order moving from the amino terminus to the carboxy terminus.

The CDR-H1 is approximately 10 to 12 residues in length and typically starts 4 residues after a Cys according to the Chothia and AbM definitions, or typically 5 residues later according to the Kabat definition. The H1 is typically followed by a Trp, typically Trp-Val, but also Trp-Ile, or Trp-Ala. The length of H1 is approximately 10 to 12 residues according to the AbM definition, while the Chothia definition excludes the last 4 residues.

The CDR-H2 typically starts 15 residues after the end of H1 according to the Kabat and AbM definitions. The residues preceding H2 are typically Leu-Glu-Trp-Ile-Gly (SEQ ID NO:8) but there are a number of variations. H2 is typically followed by the amino acid sequence Lys/Arg-Leu/Ile/Val/Phe/Thr/Ala-Thr/Ser/Ile/Ala (SEQ ID NO:9). According to the Kabat definition, the length of H2 is approximately 16 to 19 residues, where the AbM definition predicts the length to be typically 9 to 12 residues.

The CDR-H3 typically starts 33 residues after the end of H2 and is typically preceded by the amino acid sequence Cys-Ala-Arg. H3 is typically followed by the amino acid Gly. The length of H3 ranges from 3 to 25 residues The CDR-L1 typically starts at approximately residue 24 and will typically follow a Cys. The residue after the CDR-L1 is always Trp and will typically begin one of the following sequences: Trp-Tyr-Gln, Trp-Leu-Gln, Trp-Phe-Gln, or Trp-Tyr-Leu. The length of CDR-L1 is approximately 10 to 17 residues.

The CDR-L2 starts approximately 16 residues after the end of L1. It will generally follow residues Ile-Tyr, Val-Tyr, Ile-Lys or Ile-Phe. The length of CDR-L2 is approximately 7 residues.

The CDR-L3 typically starts 33 residues after the end of L2 and typically follows a Cys. L3 is typically followed by the amino acid sequence Phe-Gly-Xaa-Gly (SEQ ID NO:10). The length of L3 is approximately 7 to 11 residues.

Various methods for modifying antibodies have been described in the art. For example, U.S. Pat. No. 5,530,101 (Queen, et al.), describes methods to produce humanized antibodies wherein the sequence of the humanized immunoglobulin heavy chain variable region framework is 65% to 95% identical to the sequence of the donor immunoglobulin heavy chain variable region framework. Each humanized immunoglobulin chain will usually comprise, in addition to the CDRs, amino acids from the donor immunoglobulin framework that are, e.g., capable of interacting with the CDRs to affect binding affinity, such as one or more amino acids that are immediately adjacent to a CDR in the donor immunoglobulin or those within about 3 angstroms, as predicted by molecular modeling. The heavy and light chains may each be designed by using any one or all of various position criteria. When combined into an intact antibody, humanized immunoglobulins are substantially non-immunogenic in humans and retain substantially the same affinity as the donor immunoglobulin to the antigen, such as a protein or other compound containing an epitope. See also related methods in U.S. Pat. No. 5,693,761; Queen, et al.; U.S. Pat. No. 5,693,762; and U.S. Pat. No. 5,585,089.

In one example, U.S. Pat. No. 5,565,332 describes methods for the production of antibodies, and antibody fragments, that have binding specificity similar to a parent antibody, but which have increased human characteristics. Humanized antibodies are obtained by chain shuffling using, for example, phage display technology and a polypeptide comprising the heavy or light chain variable region of a non-human antibody specific for an antigen of interest, which is then combined with a repertoire of human complementary (light or heavy) chain variable regions. Hybrid pairings which are specific for the antigen of interest are identified and human chains from the selected pairings are combined with a repertoire of human complementary variable domains (heavy or light). In another embodiment, a component of a CDR from a non-human antibody is combined with a repertoire of component parts of CDRs from human antibodies. From the resulting library of antibody polypeptide dimers, hybrids are selected and may used in a second humanizing shuffling step; alternatively, this second step is eliminated if the hybrid is already of sufficient human character to be of therapeutic value. Methods of modification to increase human character are known in the art. See Winter, FEBS Letts. 430:92-92 (1998).

As another example, U.S. Pat. No. 6,054,297 describes a method for making humanized antibodies by substituting a CDR amino acid sequence for the corresponding human CDR amino acid sequence and/or substituting a framework region (FR) amino acid sequence for the corresponding human FR amino acid sequences. As yet another example, U.S. Pat. No. 5,766,886 describes methods for identifying the amino acid residues of an antibody variable domain that may be modified without diminishing the native affinity of the antigen binding domain, while reducing its immunogenicity with respect to a heterologous species, and methods for preparing these modified antibody variable regions for administration to heterologous species. See also U.S. Pat. No. 5,869,619.

Modification of an antibody by any of the methods known in the art is designed to achieve increased or decreased binding affinity for an antigen and/or to reduce immunogenicity of the antibody in the recipient. In one approach, humanized antibodies can be modified to eliminate glycosylation sites in order to increase affinity of the antibody for its cognate antigen (Co, et al., Mol. Immunol. 30:1361-1367 [1993]). Techniques such as "reshaping," "hyperchimerization," and "veneering/resurfacing" have produced humanized antibodies with greater therapeutic potential. Vaswami, et al., Annals of Allergy, Asthma, & Immunol 81:105 (1998); Roguska, et al., Prot. Engineer. 9:895-904 (1996)]. See also U.S. Pat. No. 6,072,035, which describes methods for reshaping antibodies. While these techniques diminish antibody immunogenicity by reducing the number of foreign residues, they do not prevent anti-idiotypic and anti-allotypic responses following repeated administration of the antibodies. Alternatives to these methods for reducing immunogenicity are described in Gilliland et al., J. Immunol. 62(6):3663-71 (1999).

In many instances, humanizing antibodies result in a loss of antigen binding capacity. It is therefore preferable to "backmutate" the humanized antibody to include one or more of the amino acid residues found in the original (most often rodent) antibody in an attempt to restore binding affinity of the antibody. See, e.g., Saldanha et al., Mol. Immunol. 36:709-19 (1999).

In the following examples, the widely accepted mouse model for human, and more generally mammalian, cardiovascular physiology is used to illustrate aspects of the invention. Example 1 provides a description of nucleic acid constructs used in generating the transgenic mice, Example 2 describes the production of transgenic mouse cell lines and the generation of transgenic mice, Example 3 discloses the analyses of transgenic mouse tissues, Example 4 details actomyosin ATPase assays, Example 5 describes in vivo left ventricular pressure assays, Example 6 addresses in vitro assays of isolated hearts, Example 7 discloses antibodies discriminating between or among cTnI forms, Example 8 describes screens for modulators of cTnI function, Example 9 provides diagnostic applications using a binding partner specific for the N-terminal domain of cTnI, and Example 10 describes cTnI polypeptide patterns in cardiac disease.

EXAMPLE 1

Construction of a cDNA Template Encoding cTnI-ND

A cDNA encoding mouse cTnI was engineered that deleted the cTnI coding region for amino acids 1-28, thus mimicking the naturally occurring proteolytic truncation. See FIG. 8 for a schematic illustration. cDNA encoding intact mouse cTnI was cloned by reverse transcription-coupled polymerase chain reaction (RT-PCR). Total RNA was extracted from ventricular muscle of an adult 129SvJ mouse using TRIzol reagent (GIBCO/BRL) according to the manufacturer's protocol. The upstream (forward) and downstream (reverse) oligonucleotide primers were synthesized according to the published mouse cTnI cDNA sequence (17) corresponding to the regions around the translation initiation and termination codons, respectively. The first strand mouse cTnI cDNA was synthesized from the total RNA preparation using avian myeloblastosis virus reverse transcriptase. Double-stranded cDNA including the entire coding region was then amplified by PCR and cloned into the pAED4 plasmid as previously described (18, incorporated herein by reference in its entirety). Full length mouse cTnI cDNA, including the 3'-untranslated regions and the poly(A) tail was then reconstituted by pasting a restriction enzyme fragment, cloned by PCR from a unidirectional mouse cardiac cDNA λ-ZAPII phage library (19) using a cTnI-specific forward primer paired with T7 primer in the downstream flanking region of the vector. The mouse cTnI cDNA was sequenced (SEQ ID NO:3) and verified by protein expression in *E. coli* and Western blot identification using an anti-TnI monoclonal antibody (monoclonal antibody, or mAb, TnI-1) (20).

To construct a cDNA encoding the N-terminally truncated cTnI, an oligonucleotide primer was synthesized to create a translation initiation codon before $Ala_{29}$ in mouse cTnI (FIG. 1A). An NdeI restriction enzyme site was included in the primer sequence for subsequent cloning. PCR-mediated mutagenesis was carried out on the full-length mouse cTnI cDNA template in the pAED4 plasmid using the N-terminal deletion primer versus a 3'-flanking primer in the vector sequences. The resulting cDNA construct was cloned into the pAED4 plasmid (FIG. 1B) and sequenced to verify fidelity of the PCR and cloning procedures. The cDNA template encoding cTnI-ND was further verified by protein expression in *E. coli* and Western blot identification using anti-TnI mAb TnI-1, as described above.

EXAMPLE 2

Production of Transgenic Mouse Lines Over-Expressing cTnI-ND in Cardiac Muscle

In order to over-express cTnI-ND in mouse cardiac muscle, a transgene was constructed using the cloned promoter of the mouse cardiac α-myosin heavy chain (α-MHC) gene (21) to direct a cardiac-specific expression of the truncated cTnI cDNA in transgenic mice. Since the cTnI N-terminal truncation is observed as a post-translational regulator of myocardial function, the α-MHC promoter, which is up-regulated in mouse hearts after birth, was used to avoid potential embryonic adaptations. The construction of the transgene is shown in FIG. 1C. The transgene DNA segment was cleaved from the recombinant plasmid by restriction enzyme digestion at flanking sites and isolated by agarose gel electrophoresis. After being recovered from the gel slice by electrophoretic elution and purified by the QIAfilter mini-column (Qiagen, Chatsworth, Calif., USA), the linear transgene DNA fragment was used in the production of transgenic mice. Using fertilized eggs from C57 mice, the pronucleus injection and embryo reimplantation were performed at the Transgenic Core Facility at Case Western Reserve University School of Medicine.

For screening of the transgenic genotypes, genomic DNA was purified from mouse tail snips by the proteinase K digestion method (22). Transgenic founders were identified by PCR using an α-MHC promoter-specific primer versus a cTnI-specific primer (FIG. 1C). The transgenic founders were bred with wild-type C57 mice and the progenies were screened by PCR as above. Positive F1 progenies from each transgenic founder line were verified for the expression of cTnI-ND in the cardiac muscle by TnI-1 mAb Western blot analysis. F2 generation with clear segregation of the transgene allele was used in this study for the characterization of cardiac function. cTnI-ND expression levels in all hearts studied were confirmed by Western blot using mAb TnI-1, as described above.

All mice were provided food and water ad libitum and placed on a 12:12-hour light-dark cycle, with the light cycle occurring during the daytime. All animal procedures were approved by the Case Western Reserve University Institutional Animal Care and Use Committee and were conducted in accordance with the Guiding Principles in the Care and Use of Animals, as approved by the Council of the American Physiological Society.

Four original cTnI-ND transgenic mouse lines were obtained with successful segregation of the transgene allele. Western blots using anti-TnI mAb TnI-1 showed cardiac-specific expression of the exogenous cTnI-ND (FIG. 2A). Similar to that previously observed in transgenic mouse hearts over-expressing slow skeletal muscle TnI (45), over-expression of cTnI-ND resulted in a significant replacement of endogenous cTnI. Densitometry of Western blots showed that in wild-type mouse hearts cTnI-ND produced by endogenous proteolysis is within a range of up to 10% of the amount of total cTnI (intact plus truncated). From the four transgenic mouse lines, two distinct groups of transgenic mouse hearts were identified with different amounts of cTnI-ND in the ventricular muscle relative to the total cTnI (FIG. 2B). Transgenic mice expressing cTnI-ND at 16-30% of total cTnI were classified as the intermediate expression group (INT-cTnI-ND) and transgenic mice expressing cTnI-ND at 41-82% of total TnI were classified as the high expression group (H-cTnI-ND). Myofibrils isolated from H-cTnI-ND hearts show that exogenous cTnI-ND is proportionally incorporated into cardiac myofilaments (FIG. 2D).

The expression level and isoform content of cardiac TnT was not affected in the transgenic mouse hearts as shown by the Western blot using mAb CT3 (FIG. 2C). The incorporation of cTnI-ND in the transgenic mouse cardiac myofibrils did not affect the incorporation of cardiac TnT (FIG. 2E), indicating integrity of the thin filaments.

Transgenic mice over-expressing various levels of cTnI-ND in the heart are apparently normal in life activities. No evidence of hypertrophy (no significant differences in heart weight/body weight ratio (Table 2) or diameter of cardiac myocytes as compared with wild type controls) and no evidence of anatomical or histological abnormality were found in the transgenic mouse hearts.

EXAMPLE 3

Verification of Cardiac-Specific Expression and Myofilament Incorporation of cTnI-ND Multiple types of somatic tissue were obtained from adult transgenic mice and homogenized in SDS-polyacrylamide gel electrophoresis (SDS-PAGE) sample buffer containing 2% SDS. The protein extracts were analyzed by SDS-PAGE and Western blot using anti-TnI C-terminus mAb TnI-1, as described (20, incorporated by reference herein), to verify cardiac-specific expression of cTnI-ND.

To examine incorporation of cTnI-ND into cardiac myofilaments, ventricular myofibrils were isolated as described [22, incorporated by reference herein] and examined by Western blotting as described above. To evaluate the effect of cTnI-ND on related myofilament proteins, the expression and myofibril incorporation of cardiac TnT in the transgenic mouse ventricular muscle was examined by Western blot analysis using a mAb CT3, as described [22, incorporated herein by reference].

The data demonstrate that the N-terminal domain of cardiac TnI is selectively removed during ischemia reperfusion of the heart. This finding establishes the diagnostic and therapeutic value of detecting the N-terminal domain, or fragment, of cTnI. For example, detection of the N-terminal domain of cTnI has value in the diagnosis of acute myocardial infarction. In addition, the N-terminal domain of cTnI is useful a marker, or indicator (e.g., diagnostic indicator) of cardiac muscle responses to stress conditions, with the presence of the N-terminal domain of cTnI correlated with beneficial effects, such as protective effects.

EXAMPLE 4

Preparation of Cardiac Myofibrils and Actomyosin ATPase Assay

Mice were anesthetized with sodium pentobarbital (50 mg/kg body weight, i.p.). Hearts removed from transgenic or control mice were perfused in a retrograde manner, either with normal saline or with saline containing 20 nM isoproterenol. Cardiac myofibrils were prepared according to the method described by Solaro et al. (23, incorporated herein by reference) with modifications. These include the use of NaF (50 mM), EGTA (2.5 mM), and $KH_2PO_4$ as phosphatase inhibitors and phenylmethylsulphonyl fluoride (0.2 mM) as a protease inhibitor (24). The ventricular muscle was pulverized in a food blender for 10 seconds in 50 ml buffer containing 0.5% (v/v) Triton X-100®, 60 mM KCl, 30 mM imidazole, pH 7.0, 2 mM $MgCl_2$, and 1 mM DTT, incubated for 5 min and centrifuged at 2,500×g for 2 min. Pellets were washed three times in buffer containing 60 mM KCl, 30 mM imidazole, pH 7.0, 2 mM $MgCl_2$, and 1 mM DTT.

Actomyosin MgATPase assays were performed to titrate the $Ca^{2+}$ sensitivity of the transgenic and wild-type mouse cardiac myofibrils under constant ionic strength, using the stability constants compiled by Fabiato (25), and were performed at pH 7.0 with 50 mM imidazole, 50 mM KCl, and 2 mM MgATP at 37° C. Inorganic phosphate release was measured as the amount of heteropolymolybdenum (26) using an automated microtiter plate reader (Bio-Rad Benchmark) for optical density at 660 nm, as described previously (27, incorporated herein by reference).

N-terminal truncation of cTnI decreases $Ca^{2+}$ sensitivity of myofibril actomyosin ATPase—The maximum $Ca^{2+}$-activated actomyosin ATPase rate was similar in cTnI-ND and WT mouse cardiac myofibrils (417±48 nmole Pi/mg protein/min and 422±73 nmole Pi/mg protein/min, respectively). Compared with myofibrils isolated from WT mouse hearts, H-cTnI-ND myofibrils were less sensitive to $Ca^{2+}$ in actomyosin ATPase assay (FIG. 3). Shown by the rightward shift of the ATPase-pCa curve, H-cTnI-ND myofibrils had significantly lower $pCa_{50}$ values compared to that of WT (5.88±0.03 versus 6.15±0.05, P<0.01). This decreased $Ca^{2+}$ sensitivity is comparable to that achieved in WT mouse controls in response to β-adrenergic stimulation. In other words, the baseline $pCa_{50}$ value for non-isoproterenol-treated H-cTnI-ND myofibrils was similar to myofibrils from isoproterenol perfused WT hearts (5.88±0.03 versus 5.91±0.05). In contrast, isoproterenol perfusion of the transgenic mouse hearts did not further decrease $Ca^{2+}$ sensitivity in H-cTnI-ND myofibrils, consistent with the absence of PKA phosphorylation sites. The results also indicate no additive effect of β-adrenergic stimulation and N-terminal truncation of cTnI, suggesting a common target for the two regulatory mechanisms.

EXAMPLE 5

Measurement of LVP Development In Vivo

Intraventricular pressure measurements were obtained in vivo using a Millar catheter (model SPR 671, Millar Instruments; Houston, Tex.) as per the method of Kass et al, (28, incorporated herein by reference) with some modification. Briefly, mice were anesthetized with sodium pentobarbital as above and a small abdominal incision was made to gain access to the mediastinum without disturbing the integrity of the thoracic cavity. An 18 gauge sheath was introduced into the left ventricle via the apex and a 1.4 French Millar catheter was introduced into the left ventricle. Intraventricular placement of the catheter was confirmed by the systolic and diastolic pressure values recorded. The micromanometer was calibrated by submerging its tip into saline (37° C.) and a pressure of 100 mmHg was applied.

Baseline in vivo parameters of H-cTnI-ND and WT mouse hearts—Table 1 summarizes the in vivo measurements obtained for WT and H-cTnI-ND mouse hearts. The heart rate was similar between WT and H-cTnI-ND mice. A small but statistically significant lower (by 13%) LVP was found in H-cTnI-ND mice compared with the WT control. In contrast, LVEDP values were much lower (by 73%) in H-cTnI-ND than the control. While no significant difference in the velocity of ventricular contraction (+dP/dt) was found between the two groups, H-cTnI-ND mouse hearts exhibited significantly faster rates of relaxation (−dP/dt) than that of WT control.

EXAMPLE 6

Functional Measurement of Isolated Working Mouse Hearts

Cardiac function of wild-type and transgenic mice were measured at 5-6 months of age using the Langendorff-Neely isolated working heart preparation, at a constant preload of 10 mmHg and an afterload of 55 mmHg, as previously described (29-31, incorporated herein by reference). Mice were anesthetized as above and the thoracic cavity was opened by a transverse incision to access the heart. Retrograde perfusion through the aorta was initiated within 60 seconds after removal of the heart. After establishing left atrial perfusion, the heart was switched to working mode. The hearts were perfused with Krebs-Henseleit bicarbonate buffer aerated with 95% $O_2$-5% $CO_2$ at 37° C. (pH=7.4). The buffer contents were as follows (in mM): 118 NaCl, 4.7 KCl, 2.25 $CaCl_2$, $MgSO_4$, 1.2 $KH_2PO_4$, 0.32 EGTA, 25 $NaHCO_3$, and 11 D-glucose (29). Functions of the isolated working hearts were measured on intrinsic beats at 37° C. with no artificial pacing applied.

Aortic flow and coronary effluent were collected once every two minutes over a 30-minute period. Heart rate and the maximum rate of pressure development (dP/dt) were measured using an MLT844 pressure transducer (Capto, Horten, Norway) attached to the aortic cannula. The analog signal was amplified with a ML 110 Bridge Amplifier (AD Instruments, Colorado Springs, Colo.), sampled at 1000 Hz by a Powerlab/16 SP digital data archiving system (AD Instruments) and stored on computer disk for subsequent analysis (29). Due to the small internal volume of the catheter/transducer system (<10 µL), the force-frequency response characteristics are adequate for measuring relative pressure derived variables with frequencies approaching 14 Hz (29).

Stroke volume (µL/g heart tissue) was calculated as the sum of aortic flow and coronary effluent, normalized to heart rate. Stroke work (mL-mmHg/g heart tissue) was calculated as stroke volume X average aortic pressure (diastolic pressure+one-third of pulse pressure) (mmHg). During the collection of aortic flow, time to peak pressure (TTP) and the relaxation times (RT) at 10, 50 and 80% total relaxation ($RT_{10}$, $RT_{50}$ and $RT_{80}$, respectively) were measured from the pressure traces. Systolic and diastolic pressure time integrals (STI, correlating with myocardial energy expenditure (31-34), and DTI, correlating with diastolic function and coronary perfusion (35-42), respectively) were calculated by integrating the systolic and diastolic portions of the pressure waves.

After baseline measurements were recorded, the cardiac response to β-adrenergic stimulation was measured by injecting pulsed volumes of perfusion medium containing increasing concentrations of isoproterenol (10, 30, and 50 nM, according to previous dose response analyses) into the left atrial perfusion tubing. Indicated by the increases in heart rates, the transit time for the injected dose to reach the heart was approximately 30 seconds. Measurements were made one minute after each injection during the plateau of the maximal response.

To evaluate the effect of cTnI-ND on myocardial diastolic function, ventricular performance was measured in isolated working mouse hearts at various preloads of 3.5, 10, 15, and 20 mmHg by altering the height of the left atrial perfusion reservoir. The low preload pressure of 3.5 mmHg represents a level lower than the average in vivo LVEDP measured in anesthetized WT mice (Table 1). The high preload pressure of 20 mmHg represents a perfusion pressure at the upper portion of the ascending limb of the Starling curve (43). During the experiments, shifts of preload were performed randomly and the hearts were allowed to stabilize for two minutes at each preload before functional measurements were performed.

Since the transgenic mice used in this study did not have any distinct coat or hood color markings, all functional experiments were performed in a blinded manner. Densitometric quantification of SDS-gel bands and Western blots was carried out using NIH Image 1.61 software. Based on an average heart weight of 0.130 g and an average heart rate of 467 beat per min, an estimated stroke volume of 139 µL per gram heart weight was predicted, based on data obtained from 60 isolated working wild type mouse hearts under the after load of 55 mmHg and preload of 10 mmHg. This value was determined from the regression equation, y=32.4x+4.2, r=0.83, where heart weight was plotted against stroke volume.

Hemodynamic values (stroke volume, relative ±dP/dt, intrinsic heart rate, pressure-time integrals, systolic and diastolic durations and peak/relaxation times) were initially tested for homogeneity of variance with a Levene test to determine if a value was parametric or non-parametric (44). Statistical significance was determined using either ANOVA (for parametric parameters) or a Kruskal-Wallis ANOVA (for nonparametric parameters). If a significant difference was identified by ANOVA, multiple comparisons for parametric data were examined with a Scheffe post hoc test. For nonparametric data, if a significant difference was identified with a Kruskal-Wallis ANOVA, multiple comparisons were performed using a Tamhane post hoc test. All statistical tests were performed with the use of SPSS statistical software. The 5% level of confidence was used for assigning statistically significant differences and all data are presented as mean±SD.

Baseline working parameters of isolated transgenic mouse hearts—The measurements are summarized in Table 2. Intrinsic heart rates of 460-470 beats per min were obtained for the isolated working hearts in all experimental groups. This near-in vivo heart rate in the absence of artificial pacing demonstrates viability of the working heart preparation. At 10 mmHg preload, stroke volumes of H-cTnI-ND hearts were significantly greater than WT and INT-cTnI-ND groups. Similar to in vivo measurements (Table 1), +dP/dt measured during working heart experiments were not significantly different among WT, INT-cTnI-ND and H-cTnI-ND groups. Consistently, the time to peak pressure (TTP) was similar among the three groups.

A comparison of -dP/dt showed that the H-cTnI-ND and INT-cTnI-ND group had significantly faster rates of relaxation than WT hearts. As derived from data shown in Table 2, H-cTnI-ND and INT-cTnI-ND hearts relaxed 24.7% and 14.5% faster than WT hearts, respectively. As a result of this increase in -dP/dt, the H-cTnI-ND hearts uniquely demonstrated a pattern of faster relaxation than contraction (Table 2). Compared to the relaxation time for WT controls, H-cTnI-ND hearts showed shorter durations throughout the entire course of relaxation ($RT_{10}$, $RT_{50}$ and $RT_{80}$) while INT-cTnI-ND hearts showed a shorter $RT_{10}$ (Table 2).

As a consequence of faster relaxation, the duration of systole measured as the time interval between the beginning of pressure generation and the rapid decrease of pressure marked by the closure of the aortic valve was significantly shorter for H-cTnI-ND and INT-cTnI-ND hearts than WT controls. Since the heart rates were similar in all groups, this abbreviated duration of systole resulted in a longer duration of diastole for the H-cTnI-ND hearts. The faster relaxation and longer diastole is consistent with the lower values of LVEDP measured in vivo (Table 1).

Unique effects of isoproterenol treatment on cTnI-ND hearts —FIG. 4A shows the response of H-cTnI-ND hearts to 10, 30 and 50 nM isoproterenol perfusion during working heart experiments. As expected, the velocity of contraction (+dP/dt) increased in all three groups in response to 10 nM isoproterenol. 30 nM and 50 nM isoproterenol perfusion data showed a plateau of this effect.

While cTnI-ND hearts had higher baseline -dP/dt than WT controls (Table 2), 10 nM isoproterenol produced the expected positive effect on WT hearts (FIG. 4B). However, the same treatment had less effect on INT-cTnI-ND hearts and no effect on H-cTnI-ND hearts. It is interesting to note that the increased -dP/dt values in WT and INT-cTnI-ND hearts produced by 10 nM isoproterenol treatment were similar to the baseline value of H-cTnI-ND hearts (2087±58 and 2040±63, respectively, versus 2102±196 mmHg-$sec^{-1}$). Nonetheless, 30 nM and 50 nM isoproterenol perfusions produced significant increases in relaxation velocity in all three groups of hearts to reach similar absolute values (FIG. 4B). This result indicates a preserved β-adrenergic potential and precludes negative changes in the β-adrenergic system of cTnI-ND hearts.

Effects of cTnI-ND on cardiac function responding to changes in preload—FIG. 5 illustrates the stroke volume produced by isolated WT and H-cTnI-ND working hearts at various preloads. Increases in preload pressure resulted in increases in stroke volume in WT and H-cTnI-ND hearts, but H-cTnI-ND hearts produced higher stroke volume than WT heart controls at all four preload pressures tested, with a greater ratio at 3.5 mmHg. The facilitated ventricular relaxation of H-cTnI-ND hearts shown by the faster –dP/dt (Table 2), may be a primary factor for a better filling of the ventricle to increase end-diastolic volume at a given preload pressure. An increased end-diastolic volume will explain the higher stroke volume produced by H-cTnI-ND hearts.

While the increased end-diastolic volume due to better ventricular relaxation will result in higher contractility according to the Frank-Starling mechanism, the similar maximum myofilament actomyosin ATPase rate, +dP/dt and systolic pressure in the WT and cTnI-ND hearts indicated that the higher stroke volume produced by cTnI-ND hearts is not likely due to an intrinsic increase of contractility. In agreement with the hypothesis that cTnI-ND hearts have an enhanced ventricular relaxation and would be more tolerant to decreases in preload pressure, the reduction of cardiac output when preload pressure was lowered from the standard experimental condition of 10 mmHg to 3.5 mmHg in isolated hearts was less severe in H-cTnI-ND mouse hearts (FIG. 5, the output was 1.86-fold more than that of WT hearts).

Overall effect of cTnI-ND on cardiac performance—Integrating the pressure wave for the duration of systole and diastole yielded values for STI and DTI, respectively (39). The H-cTnI-ND hearts showed significantly lower STI than WT controls (Table 2). Conversely, the largest DTI value was found for the H-cTnI-ND group, 19% greater than the WT control (Table 2). DTI of INT-cTnI-ND was 10% greater than the WT control (Table 2).

FIG. 6A illustrates a regression of STI against stroke work. The WT heart data showed an expected positive correlation of STI with stroke work (r=0.92). An increase in STI of 1.0 mmHg·sec corresponds to an increase in stroke work of 2.49 mL·mmHg per g heart tissue. Interestingly, the H-cTnI-ND group data deviated from this regression and clustered at the lower end of the STI scale but at the higher end of the stroke work scale. Extrapolating from the corresponding WT regression data, the H-cTnI-ND data reflect a production of 69% more stroke work, at a lower STI value. Indicating a dose response to the level of N-terminally truncated cTnI, the INT-cTnI-ND data distributed between the H-cTnI-ND and WT groups and reflected 21% more stroke work relative to the WT regression curve.

On the other hand, WT, INT-cTnI-ND and H-cTnI-ND hearts showed similar positive DTI versus stroke work relationships (r=0.90, 0.88 and 0.91, respectively). FIG. 6B illustrates a combined regression curve of DTI versus stroke work for all three groups (r=0.89) where a 1.0 mmHg·sec increase in DTI corresponds to a 3.29 mL·mmHg per g heart tissue increase in stroke work.

The in vivo and isolated working heart experiments described herein revealed that cTnI-ND hearts had a significantly faster rate of relaxation and lower left ventricular end diastolic pressure (LVEDP) compared to controls. The higher baseline relaxation rate of cTnI-ND hearts was at a level similar to that of wild type mouse hearts under β-adrenergic stimulation. The decrease in cardiac output due to lower preload (reduced filling to the chambers) was significantly smaller for cTnI-ND hearts compared to controls. These findings indicate that removal of the N-terminal extension of cTnI via restricted proteolysis enhances cardiac function by increasing the rate of myocardial relaxation and lowering LVEDP to facilitate ventricular filling, thus resulting in better utilization of the Frank-Starling mechanism.

A unique feature of the increased relaxation is an increase in cardiac output without additional energetic expenditure. The fact that deletion or phosphorylation of the cTnI N-terminal region has similar biochemical and physiological effects on cardiac muscle relaxation indicates that it is possible to produce such an effect through the binding of a small molecule to the N-terminal region of cTnI.

EXAMPLE 7

Antibodies Discriminating Between cTnI Forms

Using a synthetic peptide containing 23 amino acids (SEQ ID NO:5; GSSDAAREPRPAPAPIRRRSSNYRAY) from the N-terminal segment of human cTnI (GenBank accession #M64247) as an antigen, specific polyclonal antisera and mouse monoclonal antibodies against the cTnI N-terminal region were prepared by immunization of rabbits with the peptide conjugated to a Keyhole Limpet Hemocyanin (KLH) carrier. The specificity of the anti-cTnI N-terminal peptide antibodies have been verified by Western blots on intact versus N-terminal truncated cTnI (FIG. 12). Antibodies were obtained from two rabbits. The immune sera give an $A_{405\ nm}$ reading of 0.6-0.7 in ELISA at 1:1,000 to 1:3,000 dilutions.

To evaluate the detection of cTnI N-terminal structural modification by ELISA using anti-N-terminal peptide antibodies, the effect of protein kinase A (PKA) treatment of cTnI on the binding affinity of the ant-cTnI N-terminal region antibodies was investigated. The results provided in FIG. 13 show that PKA-catalyzed phosphorylation of cTnI resulted in significant decreases in the affinity of the two anti-cTnI N-terminal peptide antibodies that were raised against the non-phosphorylated form of the human cTnI N-terminal peptide. The results demonstrate the feasibility of using ELISA antibody epitope conformational analysis to detect structure modification in the cTnI N-terminal region.

EXAMPLE 8

Screening for Modulators of cTnI Function

Antigen-antibody interactions, including interactions involving antigenic peptides, are based on conformational fits between the antigenic epitope and the antibody variable region. The binding of a small molecule to a protein can alter the structural conformation of one or more epitopes at or near the binding site, in turn altering the binding affinity of the epitopes to their specific antibodies. Epitope affinity assays can detect such changes in binding affinity, providing a basis for detecting the binding of small molecules to protein structures of interest.

The use of polyclonal versus monoclonal antibodies in ELISA epitope conformational analysis provides some advantages over the homogeneous nature of monoclonal antibodies. A polyclonal antibody is able to detect changes in multiple epitopes on the target structure due to ligand binding. Therefore, a rabbit polyclonal antiserum raised against an N-terminal peptide of human cTnI was used for the initial screening of molecules that bind to the N-terminal region of cTnI. On the other hand, anti-cTnI monoclonal antibodies have been developed against the N-terminal peptide as well as epitopes known to be in regions distant from the N-terminal region. These monoclonal antibodies are used in ELISA epitope analyses to further select the cTnI N-terminal binding molecules for global conformational effects on cTnI structure prior to functional screenings.

To evaluate the capacity of the methods of the invention to detect overall conformational change in cTnI due to modification of the N-terminal structure, ELISA epitope analyses were undertaken using a polyclonal anti-TnI antibody RATnI raised against skeletal muscle TnI that lacks the cTnI-specific N-terminal domain (Yu et al., 2001). Protein kinase A treatment of cTnI to produce N-terminal phosphorylation at residues Ser23 and Ser24 resulted in detectable changes in binding affinity in other regions of cTnI, as shown by the decreases in affinity of both RATnI against multiple epitopes on the non-N-terminal regions of TnI (see FIG. 14). These results show that N-terminal structural modification can induce extensive allosteric changes in cTnI, consistent with a role in modulating cardiac muscle contractility.

Any screening technique or method known in the art may be used to identify molecules that bind the N-terminal region of cTnI for use in enhancing cardiac muscle relaxation. Preferred methods are the epitope affinity assays noted above. Proteolytic removal of the N-terminal 30 amino acids of cTnI enhances cardiac diastolic function. This effect is similar to the physiological effect resulting from cTnI phosphorylation at Ser23/Ser24 (in the N-terminal region of cTnI) induced by β-adrenergic stimulation. In contrast to the broad effects of β-adrenergic agonists, selective modification of the N-terminal structure of cTnI avoids many unwanted side effects. The enhancement of myocardial relaxation produces a higher cardiac output without a proportional increase in energy expenditure. Therefore, the N-terminal domain of cTnI is a suitable target for developing a new generation of drugs for the treatment of heart failure. The screens for cTnI modulators are expected to identify molecules that bind the N-terminal region of cTnI and enhance cardiac muscle relaxation.

High-Throughput Embodiment

In some embodiments, the ELISA epitope conformational analysis is implemented in a high throughput screening format to identify protein-binding molecules. Microtiter plate-based ELISA methodology is one of the most widely used enzyme immunoassays (Schuurs & van Weemen, 1977, review). Its high sensitivity, ability to simultaneously processing large numbers of samples, amenability to automation, and use of non-radioactive reagents have led to its successful application in a variety of contexts (Voller et al., 1978, review). Accordingly, this aspect of the invention is not limited to assays for binding agents, e.g., modulators, of the N-terminal domain of cTnI, but rather finds application to peptide or protein antigens in general.

ELISA methods can be classified as direct, indirect or sandwich assays. Various amplification systems may be added to the basic methods to enhance sensitivity. Generally, indirect ELISA with an antigen immobilized on, or coated on, the microtiter plate for interaction with a primary antibody and detection via an enzyme-labeled second antibody is the most commonly used method for measuring the reaction of specific antibodies to their antigens.

The antibody-antigen binding affinity is based on conformational fits between the antigenic epitope and the antibody variable region. Changes in the conformation of an antigenic epitope can alter its binding affinity to corresponding antibodies. When a protein or peptide binds to a ligand molecule, the structural conformation of the binding site and, often, nearby regions, would change, producing conformational changes in related epitope structures. Based on this mechanism, epitope affinity assays detect the binding of small molecules to a protein structure of interest.

ELISA-based methods have been developed that detect the binding of Zn(II) ions to the N-terminal region of avian breast muscle troponin T (Wang & Jin, 1998). Direct conformational changes in the Zn(II) binding sites, and secondary conformational changes in remote regions, were sensitively detected as affinity changes of specific antibodies. This methodology also detects long-range conformational changes induced by the binding of a monoclonal antibody to the N-terminal region of a recombinant troponin T protein (Jin et al., 2000a) and epitopic conformational changes in the C-terminal domain of TnI induced by $Ca^{2+}$ binding to the troponin complex (Jin et al., 2001). Similarly, this methodology detects conformational changes in multiple epitopes on calponin (a smooth muscle and non-muscle cytoskeleton regulatory protein) resulting from phosphorylation at Ser175 (Jin et al., 2000b).

Initial high-throughput screens for modulators of the function of the N-terminal domain of cTnI are expected to assess water-soluble molecules that are amenable to aqueous ELISA assays and that are amenable to aqueous-based therapeutic or pharmaceutical compositions. In one embodiment, the basic indirect ELISA method involves an initial coating of microtiter plate wells with a synthetic N-terminal peptide of human cTnI. The synthetic cTnI is coated onto 96-well microtiter plates at 100 µL per well in 50 mM sodium carbonate buffer, pH 9.6, by incubation at 4° C. overnight. Although the coating of peptides on microtiter plates is not as effective as coating with intact proteins, there is sufficient coating of various peptides (the antisera were screened by ELISA using the 23-amino-acid peptide during the immunization process) to make use of the method. After washing and blocking the remaining plastic surfaces with 1% BSA and 0.05% Tween 20 Tween® 20 in phosphate buffered saline, pH 7.4, (PBS), the immobilized cTnI N-terminal peptide is incubated with the testing molecules or candidate modulators dissolved in PBS at 10 µM at 37° C. for 1 hour. After washing away the unbound molecules, a predetermined dilution of the rabbit anti-cTnI N-terminal peptide antiserum (FIG. 12) in PBS containing 0.1% BSA is added to the plates at 100 µL per well and incubated at 37° C. for 1 hour. Following washes with PBS plus 0.05% Tween-20 (PBS-T) to remove unbound antibody, the plates are further incubated with horseradish peroxidase (HRP)-conjugated anti-rabbit IgG second antibody, followed by PBS-T washes and $H_2O_2$-2,2'-azinobis-(3-ethylbenzthiazolinesulfonic acid) (ABTS) substrate and the reaction is allowed to proceed in accordance with a standard protocol for this colorimetric assay that is known in the art. An $A_{405\ nm}$ curve for each assay well is recorded by an automated microplate reader (BioRad Benchmark). For molecules that precipitate in PBS or that are expected to react with a component of PBS, alternative buffer systems, such as Tris-HCl or imidazole-HCl, are available and suitable.

Pre-titration of the anti-cTnI N-terminal peptide antibody is used to determine a dilution for each antibody to produce an $A_{405\ nm}$ of 0.5-0.7 under the experimental conditions in the absence of a testing molecule. The binding of a molecule to the cTnI N-terminal peptide is expected to alter (most likely reduce) the binding affinity of the peptide for the polyclonal antibody and will typically result in a lower $A_{405\ nm}$ reading. The values in the linear range of enzymatic color development are used to evaluate whether the treatment of the cTnI-N-terminal peptide with a candidate modulator (testing molecule) resulted in a change in the affinity to the anti-peptide antibody. A positive result is consistent with binding between the molecule and the cTnI N-terminal region.

The most time-consuming step in the ELISA screening procedure is the dilution and addition of individual molecules into the assay wells. All other steps can be performed with multiple channel pipetting or other equipment allowing multiple, simultaneous processing steps to be performed in parallel.

It is expected that the positive molecules will constitute a small portion of the molecular libraries being screened. Therefore, one approach to significantly increase the scale of the screening is to group the molecules into 10×10 arrays, as shown in FIG. 15. Each of the 100 molecules is screened as 20 sets of mixtures containing 10 molecules each (with none of the 20 sets containing the same 10 molecules). From the results of the 20 sets, one can identify which, if any, of the 100 molecules is positive. This design is expected to increase screening efficiency 5-fold, with a concomitant increase in confirmatory power (each molecule is tested twice). A precaution in applying this approach is to make sure that the mixes of molecules will not result in chemical changes (e.g., reactions between mixed candidate modulators). It may also be necessary to adjust the total concentration of molecules in one sample to minimize nonspecific effects. One of skill in the art will recognize that the grouping of testing molecules or candidates can be based on a factor other than 10, and all such groupings are contemplated by the invention. Moreover, one of skill will recognize the general applicability of grouping candidate molecules in screens of a wide variety of types designed to reveal interactions between candidates and a wide variety of antigenic peptides or proteins of interest. The high-throughput screening method with the grouping of candidate molecules has been exemplified herein in the context of ELISA screens for modulators of the N-terminal domain of cTnI.

In some assays, a candidate modulator or testing molecule may non-specifically bind immunoglobulin, resulting in altered affinity of the anti-cTnI antibody and/or the HRP-labeled second antibody due to a false positive. To avoid, or minimize, false positives, positive molecules are examined in control ELISA assays using an unrelated antigen-antibody pair. If the control ELISA also shows that the testing molecule results in an altered, e.g. a decreased, $A_{405\ nm}$, the molecule can be avoided as a compound producing artefactual results.

Identification of candidates as modulators on the basis of binding the N-terminal region of cTnI, as detected in the ELISA with a single antibody dilution, are preferably confirmed by comparing antibody affinity titration curves in the presence versus absence of the candidate modulator or testing molecule. The ELISA is carried out as above with, e.g., five serial dilutions of the anti-cTnI N-terminal antibody (e.g., dilutions of $10^2$, $10^3$, $10^4$, $10^5$, and $10^6$). This series of dilutions has been found to be highly reliable in detecting changes in antibody affinity resulting from small molecule binding to the antigen (Wang & Jin, 1998; Jin et al., 2000b).

The cTnI N-terminal peptide binding molecules, preferably confirmed as described above, are amenable to further evaluation of binding affinity. For example, indirect ELISA as described above is performed with serial dilutions of the binding molecule (Jin & Root, 2000). The initial testing concentrations are, e.g., 100 µM, 10 µM, 1 µM, 0.1 µM, and 10 nM. After identifying the affinity range, a finer gradient is optionally examined to construct the affinity titration curve and estimate the concentration required for reaching 50% maximum binding. This information reflects the potency of the molecule in physiological and pharmacological applications.

The screening of cTnI N-terminal binding molecules will identify candidates that can induce functional changes in TnI to mimic the effect of N-terminal truncation or phosphorylation on cardiac muscle relaxation. Since the effect of cTnI N-terminal structure modification is conferred through allosteric effects on other regions of cTnI, molecules binding to the cTnI N-terminal region may be further evaluated by ELISA conformational analyses using an antibody or antibodies, e.g., the polyclonal RATnI antibody, against at least one non-N-terminal region epitope (FIG. 14). The ELISA is carried out as described above using, in one embodiment, intact cTnI protein coated onto the plates, RATnI as the first antibody, and HRP-labeled anti-rabbit IgG as the second antibody. See generally, Wang & Jin, 1998; 2000b; Jin & Root, 2000. Detection of long-range, global conformational changes upon binding of a candidate molecule to the N-terminal region is consistent with that molecule inducing functional changes in cTnI.

To maximize throughput, the ELISA assay has been described in terms of initially testing a single concentration of the candidate modulators or testing molecules. This concentration (10 µM) will identify high affinity binding ligands for future use as pharmacological reagents. One of skill in the art will recognize that this concentration of candidates can be adjusted, for example by increasing the concentration to 50-100 µM if multiple screens fail to yield a positive result. Of course, post-screen modifications of the structure of any identified modulators can be used to prepare a derivative in which the binding affinity has been altered relative to the originally identified molecule.

The conformational changes detected by ELISA epitope affinity analyses are amenable to confirmation by spectrometric measurements (Jin & Root, 2000).

Beyond screens designed to identify modulators of cTnI binding affinity, the invention comprehends assays for other physiological effects that mimic the N-terminally truncated or phosphorylated forms of cTnI. For example, actomyosin MgATPase assays are performed to titrate the $Ca^{2+}$ sensitivity of mouse cardiac myofibrils in the presence versus absence of the candidate molecules. The assays are known in the art and are carried out using conventional protocols. For example, a microtiter plate-based method may be used (Barbato et al., J. Biol. Chem. 280:6602-6609 (2005)). The assays reveal the effects of the candidate molecules on the $Ca^{2+}$ sensitivity of cardiac myofibrils. Molecules that decrease the $Ca^{2+}$ sensitivity of cTnI are identified as potential candidates that mimic the effect of physiological modifications of the cTnI N-terminal region.

The invention also contemplates modifications of modulators identified in the above-described screens. For hydrophilic compounds, e.g., modifications known in the art will be undertaken to facilitate effective penetration of the modulator into cardiac muscle cells. As an alternative, the modulators are delivered in a vehicle that will promote effective entry into the targeted cardiac muscle cells using techniques known in the art (e.g., targeted liposomes, benign viruses modified by linkage to the modulator, and the like).

Once the modulator has been engineered, if necessary, to ensure passage into the cardiac muscle cell, the effects of the modulator on cardiac function is tested in isolated working mouse hearts. The measurements may suitably be done in 5-6-month-old mice using the Langendorff-Neely isolated working heart preparation, as known in the art (see Barbato et al., J. Biol. Chem. 2005). The molecules are delivered to the working heart preparations through coronary perfusions and cardiac muscle contractility and cardiac function are recorded to evaluate the pharmacological effects of the modulator on the velocity of myocardial relaxation, cardiac output versus energy expenditure, and tolerance to decreases in pre-load, providing information useful in administering the modulator as a therapeutic to humans and/or other animals.

Any subsequent chemical modification of a modulator, for example to lower or eliminate toxicity or other side effects, are accomplished using techniques well known in the medicinal chemistry field. The effect of such modifications are readily determined using the assays disclosed herein.

EXAMPLE 9

Diagnostic Applications Using a Binding Partner Specific for the N-Terminal Domain of cTnI Using the methods described herein, an antibody was generated that specifically recognized the N-terminal domain of cardiac TnI and its affinity was significantly decreased when the N-terminal domain of cardiac TnI was phosphorylated. Through routine antibody generation techniques and screening against phosphorylated and non-phosphorylated forms of the N-terminal domain of cTnI, one of skill would be able to generate an antibody that exhibited such selective binding characteristics. More generally, one of skill would be able to identify any specific binding partner demonstrating a detectable difference in affinity for binding the phosphorylated and non-phosphorylated forms of the N-terminal domain of cTnI. These selective binding molecules are useful in screening for the relative presence of cTnI that is either phosphorylated or not phosphorylated at its N-terminus. As a control, a binding partner specific for cTnI, regardless of whether its N-terminus is phosphorylated or not, is used in some embodiments, to provide a measure of total cTnI. For example, an antibody recognizing a cTnI epitope that is not N-terminally disposed, or the natural binding partners of TnI (i.e., TnC and TnT), would be suitable.

These screening methods provide the basis for diagnostic methods designed to reveal the relative proportion of cTnI that is phosphorylated (or, conversely, non-phosphorylated), providing the basis for diagnosing a cardiac condition involves posttranslational adaptation in order to compensate for the reduced function. This development demonstrates the feasibility of our screening strategy. We have developed an ELISA-based method using this strategy to detect structural modification in the N-terminal region of cardiac TnI. This line of methods can be used in screening compounds that bind this region as potential drugs in modulating contractility.

EXAMPLE 10 cTnI Polypeptide Patterns in Cardiac Disease

Total serum cTnI has been used in the clinical diagnosis of acute myocardial infarction (AMI) by quantifying total cTnI (intact or fragments) released from the necrotic cardiac muscle cells. While total serum cTnI is recognized as a reliable quantitative indicator of infarct size, identification of specific fragments of cTnI in the serum will provide critical information for the stage of AMI and for the evaluation of the myocardial responses to the ischemia reperfusion stress conditions. The methods of the invention provide this level of information and are important diagnostic tools useful in directing effective treatments.

Langendorff-Neely isolated working heart preparations of rats (250-300 gm body weight) were used at a constant pre-load of 15 mmHg and an afterload of 60 mmHg, consistent with Barbato et al., (2005), as modified. Barbato et al., (2005) is incorporated herein by reference in its entirety. Rats were anesthetized with sodium pentobarbital (50 mg/kg body weight, i.p.) and the thoracic cavity was opened by a transverse incision to access the heart. Retrograde perfusion through the aorta was initiated within 60 seconds after removal of the heart. After establishing left atrial perfusion, the heart was switched to working mode. The hearts were perfused with Krebs-Henseleit bicarbonate buffer aerated with 95% $O_2$-5% $CO_2$ at 37° C. (pH 7.4). The buffer contents were as follows (in mM): 118 NaCl, 4.7 KCl, 2.25 $CaCl_2$, $MgSO_4$, 1.2 $KH_2PO_4$, 0.32 EGTA, 25 $NaHCO_3$, and 11 D-glucose. Functions of the isolated working hearts were measured on intrinsic beats at 37° C. with no artificial pacing applied.

Aortic flow and coronary effluent were collected once every 5 minutes over the experimental period. Heart rate and the maximum rate of pressure development (±dP/dt) were measured using an MLT844 pressure transducer (Capto, Horten, Norway) attached to the aortic cannula. The analog signal was amplified with a ML 110 Bridge Amplifier (AD Instruments, Colorado Springs, Colo.), sampled at 1000 Hz by a Powerlab/16 SP digital data archiving system (AD Instruments) and stored on computer disk for subsequent analysis.

Stroke volume (μL/g heart tissue) was calculated as the sum of aortic flow and coronary effluent, normalized to heart rate. Stroke work (mL-mmHg/g heart tissue) was calculated as stroke volume X average aortic pressure (diastolic pressure+one-third of pulse pressure) (mmHg). During the collection of aortic flow, time to peak pressure (TTP) and the relaxation times (RT) at 10, 50 and 80% total relaxation (RT10, RT50 and RT80, respectively) were measured from the pressure traces. Systolic and diastolic pressure time integrals (STI, correlating with myocardial energy expenditure, and DTI, correlating with diastolic function and coronary perfusion, respectively) were calculated by integrating the systolic and diastolic portions of the pressure waves.

Ischemia treatment was carried out by ligating the left anterior descending coronary artery in the lower or upper middle portion for 30 minutes to generate small or large areas of infarct. The ligation was then removed for 60 minutes of reperfusion. Aortic pressure and cardiac output were continuously recorded to monitor the effect of ischemia reperfusion on cardiac function. At the end of the experiments, the heart was removed and sectioned into areas representing the center of the ischemia-reperfused zone, the adjacent zone, and remote regions. The cardiac muscle samples were immediately homogenized in SDS-gel sample buffer for SDS-PAGE and Western blot analyses. The results show that while there is no apparent overall cardiac protein degradation in the infarct zone (FIG. 16), as shown by the SDS-gel, ischemia reperfusion resulted in a significant level of N-terminally truncated cTnI, as detected by the anti-cTnI C-terminal-specific monoclonal antibody TnI-1. The results also show that in the case of a small infarct, the increase in cTnI N-terminal truncation was only found in the infarcted region. In contrast, in the case of a large infarct, cTnI N-terminal truncation occurred at higher levels in the infarcted area, as well as areas outside the infarct zone, indicating a global compensatory response.

The results of these experiments thus revealed that cTnI N-terminal truncation occurred as an early and specific modification (FIG. 16). The results also indicated that the N-terminally truncated cTnI was retained in the infarcted cardiac muscle during the early period of ischemia reperfusion. The significance of this observation is two-fold. First, it indicates that release of the N-terminal fragment is an early sign of AMI and is a useful early diagnosis marker of AMI. The development of cTnI N-terminal domain-specific antibodies has contributed to the demonstration of the feasibility of this approach, as shown in the actual examples disclosed herein. Second, the N-terminally truncated cTnI is expected to provide a vital function in compensating for acutely impaired myocardial function, e.g., by improving cardiac muscle relaxation against contracture, a key factor in ischemia reperfusion injury. Accordingly, the quantification of the N-terminal truncation of cTnI versus the overall degradation of cTnI in AMI will reflect myocardial viability and prognosis for the patient. Based on the disclosures herein and the knowledge in the art, one of skill would understand how to generate a variety of N-terminal domain-specific antibodies recognizing this region of cTnI and would understand how to use any of those antibodies in the diagnostic, therapeutic, monitoring and screening methods disclosed herein.

The results of these studies establish that the N-terminal fragment of cTnI is a specific diagnostic indicator or marker for the early stage of ischemia reperfusion injury to the heart during AMI, and that the N-terminal fragment of cTnI is an indicator for the acute compensation response of the cardiac muscle to ischemia reperfusion stress and, thus, to the prognosis for a given patient or non-human animal. Also, these studies reveal that a specific 23-amino acid antigenic peptide was designed (see SEQ ID NO:5) and used to elicit polyclonal and monoclonal antibodies specifically recognizing the N-terminal region of cTnI, providing a realized example of measuring the various forms of cTnI in a diagnostically valuable way.

Based on the foregoing studies and disclosures, it is apparent that truncated cTnI provides an improved marker for the diagnosis of cardiac diseases and disorders, such as acute myocardial infarction. Accordingly, methods and kits that specifically recognize the N-terminal fragment of cTnI, or an N-terminally truncated cTnI, are contemplated by the invention. In specifically recognizing the N-terminal fragment or the truncated cTnI, it is understood that the methods and kits may provide agents that also recognize, e.g., full-length cTnI, provided that the methods and kits provide a capacity to discriminate between or among the various forms of cTnI.

All references cited herein are incorporated by reference in their entireties, and particularly for those passages pertinent to the basis for citation.

References

1. Gordon, A. M., Homsher, E., and Regnier, M. (2000) Physiol. Rev. 80, 853-924.
2. Leavis, P. C., and Gergely, J. (1984) CRC Crit. Rev. Biochem. 16, 235-305.
3. Perry, S. V. (1999) Mol. Cell. Biochem. 190, 9-32.
4. Takeda, S., Yamashita, A., Maeda, K. and Maeda, Y. (2003) Nature 424, 35-41.
5. Robertson, S. P., Johnson, J. D., Holroyde, M. J., Kranias, E. G., Potter, J. D., and Solaro, R. J. (1982) J. Biol. Chem. 257, 260-263.
6. Solaro, R. J., Holroyde, M. J., Herzig, J. W., and Peterson, J. (1980) Eur. Heart J. Suppl. A, 21-27.
7. Yu, Z. B., Zhang, L. F., and Jin J. P. (2001) J. Biol. Chem. 276, 15753-15760.
8. Bungo, M. W., Goldwater, D. J. Popp, R. L., and Sandler, H. (1987) J. Appl. Physiol. 62, 278-283.
9. Perhonen, M. A., Franco, F., Lane, L. D., Buckey, J. C., Blomqvist, C. G., Zerwekh, J. E., Peshock, R. M., Weatherall, P. T., and Levine, B. D. (2001) J. Appl. Physiol. 91, 645-653.
10. Convertino, V., and Hoffler, G. W. (1992) J. Fla. Med. Assoc. 79, 517-524.
11. Moore, T. P., and Thornton, W. E. (1987) Aviat. Space Environ. Med. 58, A91-96.
12. Parazynski, S. E., Hargens, A. R., Tucker, B., Aratow, M., Styf, J., and Crenshaw, A. (1991) J. Appl Physiol. 71, 2469-75.
13. Tomaselli, C. M., Kenney, R. A., Frey, M. A., and Hoffler, G. W. (1987) Aviat. Space Environ. Med. 58, 3-8.
14. Gaffney, F. A., Nixon, J. V., Karlsson, E. S., Campbell, W., Dowdey, A. B., and Blomqvist, C. G. (1985) Am. J. Cardiol. 56, 634-638.
15. Sangha, D. S., Han, S., and Purdy, R. E. (2001) J. Appl. Physiol. 91, 789-796.
16. Convertino, V. A., Doerr, D. F., Ludwig, D. A., and Vernikos, J. (1994) Am. J. Physiol. 266, R1962-1969.
17. Guo, X., Wattanapermpool, J., Palmiter, K. A., Murphy, A. M., and Solaro, R. J. (1994) J. Biol. Chem. 269, 15210-15216.
18. Biesiadecki, B. J., and Jin, J. P. (2002) J. Biol. Chem. 277, 18459-18468.
19. Jin, J.-P., Wang, J., and Zhang, J. (1996) Gene 168, 217-221.
20. Jin J.-P., Yang, F.-W., Yu, Z.-B., Ruse, C. I., Bond, M., and Chen, A. (2001) Biochemistry 40, 2623-2631.
21. Subramanian, A., Gulick, J., Neumann, J., Knotts, S., and Robbins, J. (1993) J. Biol. Chem. 268, 4331-4336.
22. Huang, Q.-Q., Brozovich, F. V., and Jin, J.-P. (1999) J. Physiol. 520, 231-242.
23. Solaro, R. J., Pang, D. C., and Briggs, F. N. (1971) Biochim Biophys Acta 245, 259-262.
24. Wu, L. L., Tang, C., and Liu, M. S. (2001) Am. J. Physiol. Regul. Integr. Comp. Physiol. 281, R408-416.
25. Fabiato, A. (1981) J. Gen. Physiol. 78, 457-497.
26. Fiske, C. H., and Subbarrow, Y. (1925) J. Biol. Chem. 66, 375-400.
27. Rarick, H. M., Opgenorth, T. J., von Geldem, T. W., Wu-Wong, J. R., and Solaro, R. J. (1996) J. Biol. Chem. 271, 27039-27043.
28. Kass, D. A., Saeki, A., Tunin, R. S., Recchia, F. A. (1996) Circulation. 93, 1533-1541.
29. Barbato, J. C., Mulrow, P. J., Shapiro, J. I., and Franco-Saenz, R. (2001) Hypertension 40, 130-135.
30. Gauthier, N. S., Matherne, G. P., Morrison, R. R., and Headrick, J. P. (1998) J. Mol. Cell. Cardiol. 30, 453-461.
31. Neely, J. R., Liebermeister, H., Battersby, E. J., and Morgan, H. E. (1967) Am. J. Physiol. 212, 804-814.
32. O'Rourke, M. F., and Gallagher, D. E. (1996) Hypertension. 14, S147-157.
33. Goto, Y., Slinker, B. K., and LeWinter, M. M. (1990) Circ. Res. 66, 999-1011.
34. Hisano, R., and Cooper, G. 4th (1987) Circ Res. 61, 318-328.
35. Hope, S. A., Tay, D. B., Meredith, I. T., and Cameron, J. D. (2002) Am. J. Physiol. Heart Circ. Physiol. 283, H1150-1156.
36. Mullan, B. A., Young, I. S., Fee, H., and McCance, D. R. (2002) Hypertension. 40, 804-809.
37. Chemla, D., Aptecar, E., Hebert, J. L., Coirault, C., Loisance, D., Lecarpentier, Y., and Nitenberg, A. (2000) Am. J. Physiol. Heart Circ. Physiol. 279, H122-129.
38. Ferro, G., Duilio, C., Spinelli, L., Liucci, G. A., Mazza, F., and Indolfi, C. (1995) Circ. 92, 342-347.
39. Hoffman, J. I., and Buckberg, G. D. (1978) Am. J. Cardiol. 41, 327-332.
40. Buckberg, G. D., Fixler, D. E., Archie, J. P., and Hoffman, J. I. (1972) Circ. Res. 30, 67-81.

41. Duncan, H. W., Barnard, R. J., Grimditch, G. K., Vinten-Johansen, J., and Buckberg, G. D. (1987) Basic Res. Cardiol. 82, 226-232.

42. Brazier, J., Cooper, N., and Buckberg, G. (1974) Circulation. 49, 968-977.

43. Khairallah, M., Labarthe, F., Bouchard, B., Danialou, G., Petrof, B. J., and Des Rosiers, C. (2004) Am J Physiol Heart Circ Physiol. 286, H1461-H1470.

44. Munro, B. H. ed. Statistical methods for health care research. Lippincott, New York, N.Y., 2001.

45. Fentzke, R. C., Buck, S. H., Patel, J. R., Lin, H., Wolska, B. M., Stojanovic, M. O., Martin, A. F., Solaro, R. J., Moss, R. L., and Leiden, J. M. (1999) J. Physiol. 517, 143-157.

46. Murphy, A. M., Kogler, H., Georgakopoulos, D., McDonough, J. L., Kass, D. A., van Eyk, J. E., and Marban, E. (2000) Science. 287, 488-491.

47. McDonough, J. L., Arrell, D. K., and Van Eyk, J. E. (1999) Circ. Res. 84, 9-20.

48. Biesiadecki, B. J., Schneider, K. L., Yu, Z. B., Chong, S. M., and Jin, J. P. (2004) J. Biol. Chem. 279, 13825-13832.

49. Convertino, V. A., Polet, J. L., Engelke, K. A., Hoffler, G. W., Lane, L. D., and Blomqvist, C. G. (1997) Am. J. Physiol. 273, R93-99.

50. Guyton, A. C., Jones C. E., and Coleman, T. G. (1973) Am Heart J. 86, 431-437.

51. Zhang, R., Zhao, J., and Potter, J. D. (1995) J. Biol. Chem. 270, 30773-30780.

52. Chandra, M., Dong, W. J., Pan, B. S., Cheung, H. C., and Solaro, R. J. (1997) Biochemistry. 43, 13305-13311.

53. Ward, D. G., Comes, M. P., and Trayer, I. P. (2002) J. Biol. Chem. 277, 41795-41801.

54. Layland, J., Grieve, D. J., Cave, A. C., Sparks, E., Solaro, R. J., and Shah, A. M. (2004) J. Physiol. 556, 835-847.

55. Saggin, L., Gorza, L., Ausoni, S., and Schiaffino, S. (1989) J. Biol. Chem. 264, 16299-16302.

56. Jin, J.-P. (1996) Biochem. Biophys. Res. Commun. 225, 883-889.

57. Barbato, J. C., Huang, Q.-Q., Hossain, M. M., Bond, M., and Jin, J.-P. (2005) Proteolytic N-Terminal Truncation of Cardiac Troponin I Enhances Ventricular Diastolic Function, J. Biol. Chem. 280:6602-6609 (2005).

58. Cooke, R., The mechanism of muscle contraction. CRC Crit. Rev. Biochem. 21:53-118 (1986).

59. Jin, J.-P., Chen, A., Ogut, O., and Huang, Q.-Q. (2000a) Conformational modulation of slow skeletal muscle troponin T by an $NH_2$-terminal metal-binding extension. Am. J. Physiol. Cell Physiol. 279:C1067-1077.

60. Jin, J.-P., and Root, D. D. (2000) Modulation of troponin T molecular conformation and flexibility by metal ion binding to the $NH_2$-terminal variable region. Biochemistry 39:11702-11713.

61. Jin, J.-P., Walsh, M. P., Sutherland, C., and Chen, W. (2000b) A role for serine-175 in modulating the molecular conformation of calponin. Biochem. J. 350:579-588.

62. Kohler, G., and Milstein, C. (1975) Continuous cultures of fused cells secreting antibody of predefined specificity. Nature 256, 495-497.

63. Schuurs A H, Van Weemen B K. (1977) Enzyme-immunoassay. Clin Chim Acta. 81:1-40.

64. Voller A, Bartlett A, Bidwell D E. (1978) Enzyme immunoassays with special reference to ELISA techniques. J Clin Pathol. 31:507-20.

65. Wang, J., and Jin, J.-P. (1998) Conformational modulation of troponin T by configuration of the $NH_2$-terminal variable region and functional effects. Biochemistry 37:14519-14528.

66. Metzger et al., J. Cell. Biol. 126:701-711 (1994)

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features set forth herein and as follows in the scope of the appended claims.

I claim:

1. A method for monitoring cardiac function comprising measuring the level of a cardiac troponin I polypeptide selected from the group consisting of N-terminally truncated cardiac troponin I, an N-terminal fragment of cardiac troponin I and a modified cardiac troponin I in a patient.

2. The method according to claim 1 wherein the measuring comprises contacting a sample from the patient with an antibody specifically recognizing the peptide consisting of the sequence set forth in SEQ ID NO:5 and determining the level of binding of the antibody to the sample.

3. The method according to claim 1 wherein said measurement determines the relative proportion of cardiac troponin I that is truncated.

4. The method according to claim 1 wherein said cardiac troponin I polypeptide is measured in a blood sample from said patient.

5. The method according to claim 1 wherein said N-terminally truncated cardiac troponin I comprises SEQ ID NO:2 but lacks an N-terminal sequence selected from the group consisting of amino acid residues 1-26 of SEQ ID NO:2, residues 1-27 of SEQ ID NO:2 and residues 1-30 of SEQ ID NO:2.

6. The method according to claim 1 wherein the truncated cardiac troponin I is truncated human cardiac troponin I.

7. The method according to claim 1, wherein the N-terminal fragment of cardiac troponin I consists essentially of residues 1-26 of SEQ ID NO:2, residues 1-27 of SEQ ID NO:2, or residues 1-30 of SEQ ID NO:2.

8. The method according to claim 1, wherein the modified cardiac troponin I is a phosphorylated cardiac troponin I.

9. The method according to claim 8, wherein the phosphorylated cardiac troponin I is phosphorylated at position 23 or 24 of SEQ ID NO:2, or at both positions 23 and 24 of SEQ ID NO:2.

10. The method according to claim 1, wherein the modified cardiac troponin I is a cardiac troponin I comprising the amino acid sequence of SEQ ID NO: 2 with an amino acid replacement at position 23 or 24 of SEQ ID NO:2, or at both positions 23 and 24 of SEQ ID NO:2.

11. The method according to claim 10, wherein the amino acid replacement comprises a Ser replaced with another polar amino acid.

12. The method according to claim 11, wherein the other polar amino acid is a negatively charged amino acid.

13. The method according to claim 1, wherein the modified cardiac troponin I comprises an exogenous molecule non-covalently bound to a binding site within residues 1-30 of SEQ ID NO:2.

14. The method according to claim 13, wherein the exogenous molecule is a small molecule or a peptide.

15. A method of diagnosing a cardiac disease or disorder, comprising measuring the level of a cardiac troponin I polypeptide selected from the group consisting of N-terminally truncated cardiac troponin I, an N-terminal fragment of cardiac troponin I and a modified cardiac troponin I in a patient.

16. The method according to claim 15, wherein the cardiac disease or disorder is acute myocardial infarction.

17. The method according to claim 16, wherein the N-terminally truncated cardiac troponin I comprises SEQ ID NO:2 but lacks an N-terminal sequence selected from the group consisting of amino acid residues 1-26 of SEQ ID NO:2, residues 1-27 of SEQ ID NO:2 and residues 1-30 of SEQ ID NO:2.

18. The method according to claim 15, wherein the N-terminal fragment of cardiac troponin I consists essentially of residues 1-26 of SEQ ID NO:2, residues 1-27 of SEQ ID NO:2, or residues 1-30 of SEQ ID NO:2.

19. A method of developing a prognosis for a patient experiencing acute myocardial infarction, comprising measuring the level of a cardiac troponin I polypeptide selected from the group consisting of N-terminally truncated cardiac troponin I, an N-terminal fragment of cardiac troponin I and a modified cardiac troponin I in the patient.

20. The method according to claim 19, comprising comparing the level of the N-terminally truncated cardiac troponin I, the N-terminal fragment of cardiac troponin I, or the modified cardiac troponin I to the overall degradation of cardiac troponin I.

* * * * *